(12) United States Patent
Mandal et al.

(10) Patent No.: US 8,637,679 B2
(45) Date of Patent: Jan. 28, 2014

(54) PROCESS FOR THE ISOLATION OF ORGANIC COMPOUNDS USEFUL FOR THE TREATMENT OF CANCER

(75) Inventors: Chitra Mandal, Kolkatta (IN); Bikas Chandra Pal, Kolkatta (IN); Kaushik Bhattacharya, Kolkatta (IN); Suman Kumar Samanta, Kolkatta (IN); Sayantani Sarkar, Kolkatta (IN); Ranjita Das, Kolkatta (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 13/416,930

(22) Filed: Mar. 9, 2012

(65) Prior Publication Data

US 2013/0065932 A1 Mar. 14, 2013

(30) Foreign Application Priority Data

Mar. 11, 2011 (IN) .............................. 690/DEL/2011

(51) Int. Cl.
C07D 491/052 (2006.01)
(52) U.S. Cl.
USPC .......................................................... 548/421
(58) Field of Classification Search
USPC .......................................................... 548/421
See application file for complete search history.

(56) References Cited

U.S. PATENT DOCUMENTS

2010/0297760 A1 11/2010 Sinha et al.

FOREIGN PATENT DOCUMENTS

| WO | WO-2007/026203 A1 | 3/2007 |
|---|---|---|
| WO | WO 2008/051523 A2 * | 5/2008 |
| WO | WO-2010/019271 A1 | 2/2010 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Bhattacharya et al., "Apoptotic effects of mahanine on human leukemic cells are mediated through crosstalk between Apo-1/Fas signaling and the Bid protein and via mitochondrial pathways," *Biochem. Pharmacol.* 79:361-372 (2010).
Jagadeesh et al., "Mahanine reverses an epigenetically silenced tumor suppressor gene RASSF1A in human prostate cancer cells," *Biochem. Biophys. Res. Commun.* 362:212-217 (2007).
Roy et al., "Mahanine, a carbazole alkaloid from *Micromelum minutum*, inhibits cell growth and induces apoptosis in U937 cells through a mitochondrial dependent pathway," *Br. J. Pharmacol.* 145:145-155 (2005).
Roy et al., "Mechanism of mahanin-induced apoptosis in human leukemia cells (HL-60)," *Biochem. Pharmacol.* 67:41-51 (2004).
Sinha et al., "Mahanine inhibits growth and induces apoptosis in prostate cancer cells through the deactivation of Akt and activation of caspases," *Prostate* 66:1257-1265 (2006).

* cited by examiner

*Primary Examiner* — Shawquia Young
(74) *Attorney, Agent, or Firm* — Clark & Elbing LLP

(57) ABSTRACT

The present invention relates to two main components, mahanine and mahanimbine (dehydroxy-mahanine) from *Murraya koenigii* for the treatment of glioblastoma and cervical carcinoma. Mahanimbine exhibited anti-cancer activity against lymphoid leukemia, myeloid leukemia, glioma, cervical carcinoma, pancreatic, colon and lung cancers in nineteen cells of different genetic status. C-3 hydroxy and NH groups are responsible contributing groups for their cytotoxicity. Mahanine reduced the doses of cisplatin and paclitaxel in cervical cancer showing better efficacy and useful as an adjunct chemotherapeutic agent to reduce toxicity these two drugs. A new cheap process for this preparation was established. EtOAc extract containing alkaloids enriched with mahanimbine and mahanine, is active against glioma and cervical cancers. Mahanine is targeting the chaperone Hsp90 which led to the proteasome-dependent degradation of several Hsp90-client proteins in diverse carcinoma types, glioblastoma, cervical carcinoma and pancreatic adenocarcinoma irrespective of their tissue origins thereby killing the cancer cells.

10 Claims, 21 Drawing Sheets
(2 of 21 Drawing Sheet(s) Filed in Color)

| IC$_{50}$ by MTT assay, 48 hrs | | |
|---|---|---|
| Cell lines | Genetic information | IC$_{50}$ (µM) |
| U87MG | wt EGFR, wt p53, mu PTEN, del p16 | 13.4 |
| U373MG | wt EGFR, mu p53, mu PTEN | 16.8 |
| LN229 | wt EGFR, mu p53, wt PTEN, del p16 | 13.7 |
| A172 | wt EGFR and truncated 190 kDa EGFR, mu p53, del PTEN | 11.6 |
| T98G |  | 16.1 |
| U87MGEGFRvIII | vIII mutation of EGFR, wt p53, mu PTEN, del p16 | 14.1 |

| R1 | R2 | Compounds |
|---|---|---|
| OH | H | Mahanine |
| O-Me | H | Me-Mahanine |
| Biotin | H | Biotinylated –Mahanine |
| H | H | Dehydroxy-Mahanine |
| H | Me | Me-Dehydroxy-Mahanine |

| Cell lines | Dose (μM) | Viability (%) by MTT assay, 24 hrs. | | | |
|---|---|---|---|---|---|
| | | Mahanine | Dehydroxy-Mahanine | Me-Mahanine | Me-Dehydroxy-Mahanine |
| Cervical Carcinoma (HeLa) | 0 | 100 | 100 | 100 | 100 |
| | 15 | 75 | 80 | 91 | 94 |
| | 30 | 32 | 73 | 90 | 84 |
| | 50 | 14 | 43 | 65 | 81 |
| Glioblastoma (T98G) | 0 | 100 | 100 | 100 | 100 |
| | 15 | 40 | 88 | 90 | 95 |
| | 30 | 24 | 75 | 78 | 90 |
| | 50 | 15 | 39 | 64 | 82 |

| Sample | Concentration of Mahanine(mg/g or mg/ml) | Concentration of Dehydroxy-Mahanine(mg/g or mg/ml) |
|---|---|---|
| Methanolic Extract | 215.5 mg/g of MeOH extract | 31.8 mg/g of MeOH extract |
| EtOAc Fraction | 329.6 mg/g of EtOAc extract | 60.9 mg/g of EtOAc extract |
| Isolated Mahanine | 0.5±0.01 mg/ml | - |
| Isolated Dehydroxy-Mahanine | - | 5.0±0.02 mg/ml |

Figure 13

| Pk # | Retention Time | Area | Area % | Height | Height % |
|---|---|---|---|---|---|
| 1 | 3.872 | 213527 | 0.811 | 17953 | 1.474 |
| 2 | 4.565 | 5024198 | 19.089 | 300045 | 24.637 |
| 3 | 5.173 | 3545379 | 13.470 | 237886 | 19.533 |
| 4 | 6.304 | 2159340 | 8.204 | 117935 | 9.684 |
| 5 | 7.125 | 3618731 | 13.749 | 143138 | 11.753 |
| 6 | 7.808 | 49789 | 0.189 | 3498 | 0.287 |
| 7 | 8.267 | 51444 | 0.195 | 3162 | 0.260 |
| 8 | 8.821 | 44299 | 0.168 | 2034 | 0.167 |
| 9 | 10.229 | 133182 | 0.506 | 5701 | 0.468 |
| 10 | 11.083 | 805035 | 3.059 | 33332 | 2.737 |
| 11 | 11.851 | 10117750 | 38.441 | 343047 | 28.168 |
| 12 | 14.485 | 298685 | 1.135 | 6437 | 0.529 |
| 13 | 19.349 | 258717 | 0.983 | 3713 | 0.305 |

| Totals | | | | | |
|---|---|---|---|---|---|
| | | 26320076 | 100.000 | 1217881 | 100.000 |

PROCESS FOR THE ISOLATION OF ORGANIC COMPOUNDS USEFUL FOR THE TREATMENT OF CANCER

CROSS-REFERENCE TO RELATED APPLICATIONS

This application claims priority from Indian patent application no. 0690/DEL/2011 filed Mar. 11, 2011, the disclosure of which is incorporated by reference in its entirety.

FIELD OF THE INVENTION

This invention relates to an improved process for the extraction of organic compounds mahanine and dehydroxymahanine followed by isolation of mahanine and dehydroxymahanine in high yield, from the leaves or any other plant part of *Murraya koenigii*. The present invention further relates to purified herbal and non-toxic pharmaceutical molecules mahanine and mahanimbine, useful for the treatment of glioma and cervical cancers. More particularly, the present invention further relates to Mahanimbine (dehydroxy-mahanine), useful for inhibiting cell proliferation against seven different types of cancer (glioma, cervical carcinoma, lymphoid leukemia, myeloid leukemia, pancreatic cancer, colon cancer and lung cancer) in nineteen different cancer cell lines. The present invention also relates to Mahanine useful for inhibiting cell proliferation against two different types of cancer (glioma and cervical) in six different cancer cell lines. In addition, the present invention also relates to the combination therapy of Mahanine and Mahanimbine reduce the dose of highly toxic known anti-cancer agents. The present invention further relates to mahanine as a potent Hsp90 inhibitor.

BACKGROUND AND PRIOR ART OF THE INVENTION

References may be made to Journal "*Biochem Pharmacol.* 79:361-72", wherein apoptotic effects of mahanine on human leukemic cells mediated through crosstalk between Apo-1/Fas signaling and the Bid protein and via mitochondrial pathways has been reported. Mahanine is a very potent antileukemic compound in vivo and in vitro with minimal toxicity towards Balb/c and NIH (nu/nu) nude mice. In another orthotopic nu/nu mouse model, the compound showed strong anticancer activity against pancreatic cancer. Both these mouse model studies strongly support the in vivo efficacy of mahanine against cancer cells. Mahanine has minimum toxic effects in vivo indicating that mahanine is non-toxic towards nonspecific tissues of athymic nude mice model. Additionally, in vivo testing of mahanine did not show any adverse change in total body mass of normal Balb/c and athymic nude mice model. Additionally, an apoptotic pathway and a novel mechanism induced by mahanine on human leukemic cells are mediated through crosstalk between Apo-1/Fas signaling and the Bid protein and via mitochondrial pathways has established.

References may be made to Journal "*J Agric Food Chem.* 47: 444-47", wherein it is reported that the acetone extract of the fresh leaves of *Murraya koenigii* resulted in the isolation of three bioactive carbazole alkaloids, mahanimbine, murrayanol and mahanine. All three compounds were found to be mosquitocidal and antimicrobial, and exhibited topoisomerase I and II inhibitory activities.

References may be made to Patent Publication No. and Journal "WO/2008/051523 A2 and *Biochem Biophys Res Commun.* 362:212-17", wherein it was reported that mahanine is an activator of epigenetically suppressed tumor suppressor gene RASSF1A in a selected cancer cell lines [i.e., epidermoid (A431), lung (A549), pancreatic (ASPC-1), colon (HT-29), breast (MCF7), androgen-responsive (LN-CaP) and androgen-negative (PC3) prostate and ovarian (SKOV-3) cells], where RASSF1A was not expressed.

References may be made to Patent Publication No. WO2010019271, wherein a method for the treatment of cancer in a subject comprising administering a dansyl-carbazole compound has been provided. The compounds are useful for treating a cancer in a subject; suppressing the growth of a cell; rand educing DNA methyltransferase activity in a cell.

References may be made to Journal "*J Med Chem* 53:2376-82", wherein it is also reported that a fluorescent carbazole analogue of mahanine was designed and synthesized which can up-regulate RASSF1A in vitro, and thus potently inhibited human prostate cancer cell proliferation, and fluoresced at a visible wavelength, allowing for the observation of intracellular distribution and 10 mg/kg dose reduced human xenograft tumor volume by about 40%.

References may be made to Patent Publication No. and Journal "WO/2007/026203 and *Prostate.* 66:1257-65", wherein it was established that mahanine is an inhibitor of serine/threonine kinase Akt and inducer of apoptosis in prostate cancer cell line PC-3 and LNCaP.

References may be made to Journals "*Phytomedicine* 13:359-65, *Biochem Pharmacol.* 67:41-51 and *Br J. Pharmacol.* 145:145-55", wherein it is also reported that mahanine can induce apoptosis towards promyelocytic leukemic cells (HL60) and histiocytic leukemia (U937).

References may be made to Journal "*Indian J Physiol Pharmacol.* 48:348-52", wherein it was reported the hypoglycemic effect of the aqueous extract and the methanol extract of *Murraya koenigii* Spreng leaves. Daily oral administration of aqueous extract (600 mg/kg body wt.) and methanol extract (200 mg/kg body wt.) of *Murraya koenigii* Spreng leaves significantly elevated plasma insulin level in treated group than that of the control.

References may be made to Journal "*Nat Prod Commun.* 4:1089-92", wherein it is reported that three extracts (DCM, EtOAc and MeOH) of *Murraya koenigii* (L.) Spreng leaves (Rutaceae) exhibited pancreatic antilipase activity greater than 80%.

References may be made to Journal "*J Agric Food Chem.* 49:5589-94", wherein it is reported that the antioxidant activity of the leaf-extracts of *Murraya koenigii* using different solvents were evaluated based on the oil stability index (OSI) together with their radical scavenging ability against 1-1-diphenyl-2-picrylhydrazyl (DPPH).

References may be made to Journal "*Fitoterapia,* 81:1129-33", wherein it is also reported that *Murraya koenigii* (L.) Spreng leaf-extract has anti-obesity and lipid lowering effects and mahanimbine also significantly lowered the body weight on high fat diet induced obese rats.

Glioma

A glioma is a type of tumor that starts in the brain or spine. It is called a glioma because it arises from glial cells. The most common site of glioma is the brain. The exact causes of glioma are not known. Hereditary genetic disorders such as neurofibromatoses (type 1 and type 2) and tuberous sclerosis complex are known to predispose to their development. Individuals who were obese during adolescence have a three to four times greater risk of developing glioma than do individuals of normal weight during adolescence. Being tall also increases the risk; each 10-centimeter increase in height increases the risk nearly 20 percent. The molecular factors are also involved in this disease; TP53, EGFR, PDGFR and PTEN mutation are most well known alteration in this disease. EGFRvIII is the most lethal and oncogenic mutation in glioma. Gliomas cannot be cured. The prognosis for patients with high-grade gliomas is generally poor, and is especially so for older patients. Of 10,000 Americans diagnosed each year with malignant gliomas, about half are alive for 1 year after diagnosis, and 25% after two years. Those with anaplastic astrocytoma survive about three years. Glioblastoma multiforme has a worse prognosis with less than a 12-month survival after diagnosis. Temozolomide is an orally active alkylating agent that is used for persons newly diagnosed with glioblastoma multiforme. The United States Food and Drug Administration (FDA) approved it in March 2005. Studies have shown that the drug was well tolerated and provided a survival benefit. Adjuvant and concomitant temozolomide with radiation was associated with significant improvements in median progression-free survival over radiation alone (6.9 vs 5 month), overall survival (14.6 vs 12.1 month), and the likelihood of being alive in 2 years (26% vs 10%). MGMT is a DNA repair enzyme that contributes to temozolomide resistance. Methylation of the MGMT promoter, found in approximately 45% of glioblastoma multiformes, results in an epigenetic silencing of the gene, decreasing the tumor cell's capacity for DNA repair and increasing susceptibility to temozolomide. When patients with and without MGMT promoter methylation were treated with temozolomide, the groups had median survivals of 21.7 versus 12.7 months, and 2-year survival rates of 46% versus 13.8%, respectively. O-6-benzylguanine, carmustine (BCNU) and cis-platinum (cisplatin) have been the primary chemotherapeutic agents used against malignant gliomas. A small proportion of glioblastomas responds to gefitinib or erlotinib (tyrosine kinase inhibitors). A major hindrance to the use of chemotherapeutic agents for brain tumors is the fact that the blood-brain barrier (BBB) effectively excludes many agents from the CNS. For this reason, novel methods of intracranial drug delivery are being developed to deliver higher concentrations of chemotherapeutic agents to the tumor cells while avoiding the adverse systemic effects of these medications.

Cervical Cancer

Cervical cancer is the second most common malignancy among women worldwide. Every year 529,409 new cases of cervical cancer are diagnosed globally and it is responsible for 274,883 deaths. Cervical cancer comprises 13% of all cancers in women. In India, cervical cancer ranks as the first most frequent cancer among women. The cancer mostly affects women between 15 and 44 years of age and especially those from the lower economic status who fail to carry out regular health check-ups due to financial inadequacy.

Human papilloma virus infection with high risk type is main factor for the development of cervical cancer. There are 15 subtypes of high-risk type HPV strains, among which types 16 and 18 are mainly responsible for 70% of all cervical cancers and 76.7% in Indian women (Lowy D R, Schiller J T. (2006) Prophylactic human papillomavirus vaccines. *J. Clin. Invest.* 116 (5): 1167-73). High-risk HPV types encode two oncogenes, E6 and E7 that can immortalize cervical epithelial cells. E6 binds to and degrades the p53 regulatory protein, while E7 interacts with members of the retinoblastoma family. This abrogates apoptosis and cell cycle checkpoint function to enhance cell proliferation (Desaintes C, Goyat S, Garbay S, Yaniv M, Thierry F. (1999) Papillomavirus E2 induces p53-independent apoptosis in HeLa cells. *Oncogene,* 18, 4538-4545).

According to U.S. Food and Drug Administration, the standards of treatment of cervical cancer include radiation therapy, chemotherapy and surgery. Chemotherapy uses either cisplatin alone or combination of two drugs, hycamtin (topotecan hydrochloride) and cisplatin depending on the stage of cancer. But this combinational therapy is associated with high risk of neutropenia, thrombocytopenia, and anemia. Less serious side effects include nausea and vomiting, rash, and liver toxicity. Although patient survival is favorable in early-stage cervical cancer, patients in advanced stages suffer greatly resulting in a 5-year survival rate of about 20-40%.

For prevention of cervical cancer two HPV vaccines, Gardasil and Cervarix are currently used in the market. Gardasil can prevent infection against HPV types 6, 11, 16, 18 whereas; cervarix is a vaccine against HPV types 16 and 18. Both vaccines are given in three doses i.e. on 0, 1, 6 months. The costs of gardasil and cervarix are Rs.2800/dose and Rs.3200/dose respectively.

Precautions for Using Vaccines are as Follows:
  i. Both are preventative vaccines and do not treat HPV infection or cervical cancer. The U.S. Food and Drug Administration (FDA) recommend vaccination before adolescence and potential sexual activity.
  ii. These vaccines are recommended for women who are 9 to 25 years old who have not been exposed to HPV. The vaccines have been shown to be effective for at least 4 to 6 years.
  iii. Side effects of Gardasil may include joint and muscle pain, fatigue, physical weakness, general malaise and dizziness.
  iv. Gardasil cannot be taken in an allergic reaction after getting a dose of Gardasil or a severe allergic reaction to yeast, amorphous aluminum hydroxyphosphate sulfate, polysorbate.
  v. Gardasil is not recommended for pregnant women, have immune problems, like HIV infection, cancer, or in fever over 100° F.

Pancreatic Cancer

Pancreatic cancer is the fourth leading cause of death among both men and women, comprising 5% of all cancer-related deaths. The incidence of pancreatic cancer has risen slowly over the years. The disease is notoriously difficult to diagnose in its early stages. At the time of diagnosis, 52% of all patients have distant disease and 26% have regional spread. The relative 1-year survival is only 24% and the overall 5-year survival rate for this disease is less than 5%. Pancreatic cancers can arise from both the exocrine and endocrine portions of the pancreas. Of pancreatic tumors, 95% develop from the exocrine portion of the pancreas, including the ductal epithelium, acinar cells, connective tissue, and lymphatic tissue.

Hsp90 and Cancer

Hsp90, are the housekeeping proteins, mainly aid the folding of the nascent proteins. The chaperonic activity of Hsp90 promotes the function of several key signaling proteins by stabilizing themselves and endorses the abnormal proliferation of malignant cells locally, help them to migrate from restricted niche, to escape the effects of chemotherapeutic drugs, and to override their own intracellular abnormality (Whitesell L, Lindquist S L. Hsp90 and the chaperoning the cancer. *Nat Rev Cancer.* 2005 October; 5(10): 761-72). There is a review discussed these recent advances in the understanding of tumor Hsp90 for the treatment and diagnosis of cancer. Additionally, the role of Hsp90 in non-oncological diseases was discussed by Kamal et al., ((2004) Therapeutic and diagnostic implications of Hsp90 activation. *Trends Mol. Med.* 10:283-90). For another review discussing the discovery and development of novel heat shock protein 90 small-molecule inhibitors by targeting multiple signalling pathways, as well as the alternative approaches to inhibit HSP90 activity, see, for example, Powers M V and Workman P ((2006) Targeting of multiple signalling pathways by heat shock protein 90 molecular chaperone inhibitors. *Endocr Relat Cancer.* 13: S125-35).

This chaperonic protein has flexible characteristics to attach with different co-chaperones depending upon the energy execution (Neckers L. Heat shock protein 90: the cancer chaperone. (2007) *J Biosci.* April; 32(3): 517-30). In cancer cells, Hsp90 serves an immense role for survival of the malignant cells and being constitutively expressed more or less about 10 fold higher than that of the normal cells signifying the crucial role of this protein in growth and survival of malignant cells (Isaacs J S, Xu W, Neckers L. Heat shock protein 90 as a molecular target for cancer therapeutics. (2003) *Cancer Cell.* March; 3(3):213-17). There is also a documentation which enclosed the Hsp90 is a novel anticancer target (Neckers L, Mimnaugh E, Schulte T W. (1999) Hsp90 as an anti-cancer target. *Drug Resist Updat.* 2:165-72). In a review authors have also discussed the mechanism-based use of Hsp90 inhibitors, both alone and in combination with other drugs, should augment the treatment of multiple forms of cancer (Neckers L, Ivy S P. (2003) Heat shock protein 90. *Curr Opin Oncol.* 15: 419-24). There is also a review which summarizes recent literature implicating Hsp90 as a key facilitator for the maturation of proteins represented in all six hallmarks of cancer: i) growth signal self-sufficiency, ii) antigrowth signal insensitivity, iii) evasion of apoptosis, iv) unlimited replicative potential, v) metastasis and tissue invasion, and vi) sustained angiogenesis. This review also described the recent advances towards the development of novel Hsp90 inhibitors via structure-based drug design that have contributed to the number of compounds undergoing clinical development (Bishop S C, Burlison J A, Blagg B S. (2007) Hsp90: a novel target for the disruption of multiple signaling cascades. *Curr Cancer Drug Targets* 7:369-88).

It is a great promise to identify, characterize or customize the new chemotherapeutic agents by targeting specific cellular protein(s) or event. The group of compounds like benzoquinone ansamycins (geldanamycin, 17-AAG) is proved to be potent Hsp90 inhibitor. 17-AAG shows inhibitory effects in colon, breast and prostate cancer xenograft models (Basso A D, Solit D B, Munster P N, Rosen N. Ansamycin antibiotics inhibit Akt activation and cyclin D expression in breast cancer cells that overexpress HER2. *Oncogene.* 2002 Feb. 14; 21(8): 1159-66; Kelland L R, Sharp S Y, Rogers P M, Myers T G, Workman P. DT-Diaphorase expression and tumor cell sensitivity to 17-allylamino, 17-demethoxygeldanamycin, an inhibitor of heat shock protein 90. *J Natl Cancer Inst.* 1999 Nov. 17; 91(22):1940-49; Solit D B, Zheng F F, Drobnjak M, Münster P N, Higgins B, Verbel D et al. 17-Allylamino-17-demethoxygeldanamycin induces the degradation of androgen receptor and HER-2/neu and inhibits the growth of prostate cancer xenografts. *Clin Cancer Res.* 2002 May; 8(5): 986-93). Macrolide group (Radicicol and derivatives) also established as effective Hsp90 inhibitor (Neckers L. Development of small molecule Hsp90 inhibitors: utilizing both forward and reverse chemical genomics for drug identification. *Curr Med. Chem.* 2003 May; 10(9):733-9). The other chemical groups like pyrazoles, isoxazoles, sulfanyl analogues, resorcinol bearing compounds block the N-terminal ATP binding pocket of Hsp90. Novobiocin along with its derivatives and cisplatin can block the C-terminal ATP binding pocket (Janin Y L. Heat shock protein 90 inhibitors. A text book example of medicinal chemistry? *J Med. Chem.* 2005 Dec. 1; 48(24):7503-12; Taldone T, Sun W, Chiosis G. Discovery and development of heat shock protein 90 inhibitors. *Bioorg Med. Chem.* 2009 Mar. 15; 17(6):2225-35; Powers M V, Workman P. Inhibitors of the heat shock response: biology and pharmacology. *FEBS Lett.* 2007 Jul. 31; 581(19):3758-69). References may be made to Journal "Pearl L H. (2005) Hsp90 and Cdc37—a chaperone cancer conspiracy. *Curr Opin Genet Dev.* 15:55-61" wherein a review discussed on the emerging role of Cdc37 as a key component of the Hsp90 molecular chaperone system and described its particular responsibility for enabling protein kinase oncogenes to do their damage.

References may be made to Journal "*Mol Cancer Ther.* 7:162-70", wherein it was shown that celastrol disrupted Hsp90-Cdc37 interaction in the superchaperone complex to exhibit antitumor activity in vitro and in vivo.

References may be made to Journal "*Cancer Res.* 67:11942-50", wherein it was shown that Cdc37 is essential for maintaining prostate tumor cell growth and may represent a novel target in the search for multi-targeted therapies based on the HSP90 chaperone system.

References may be made to Journal "*J Med. Chem.* 49:7721-30", wherein a nonpeptidic small molecule, 5-aminoimidazole-4-carboxamide-1-beta-D-ribofuranoside (AICAR), was identified as a structurally novel inhibitor of Hsp90. The compound is selected to bind the Hsp90 N-terminal domain.

References may be made to journal "*J. Agric. Food Chem.*, 2001, 49 (11), pp 5589-5594", wherein antioxidative properties of the leaves extracts of *Murraya koenigii* using different solvents were evaluated based on the oil stability index (OSI) together with their radical scavenging ability against 1-1-diphenyl-2-picrylhydrazyl (DPPH). Five carbazole alkaloids were isolated from the $CH_2Cl_2$ extract and their structures were identified to be euchrestine B (1), bismurrayafoline E (2), mahanine (3), mahanimbicine (4), and mahanimbine (5) based on $^1H$ and $^{13}C$ NMR and mass (MS) spectral data. In this process, initial extraction was done by Acetone. Seven different fractionations were separated by vacuum liquid chromatography (VLC). Selection of bioactive fractions was done from seven different fractions. Bioactive fractions were further separated by Medium pressure liquid chromatography (MPLC) to isolate five more fractions. Selection of bioactive fractions was done from these five different fraction. The bioactive fraction was finally purified by preparative thin layer chromatography (PTLC). Yield of pure compounds is 4.26 mg per gm of acetone extract. However, in the present invention, initial extraction was done by MeOH. Total alkaloids were isolated by chloroform, precipitated with acid-base and dissolved in ethyl acetate. Pure compounds were purified by silica gel column chromatography. Yield of pure compounds is ~41 mg from 1.0 gm of MeOH extract.

In summary, the major drawbacks of the hitherto known processes described herein above for the extraction of mahanine and mahanimbine are:

1) Leads to many more steps for actual identification of active alkaloids.
2) Several costly chromatography processes (VLC, MPLC, PTLC).
3) Consumes lots of solvents.
4) Many fractions (more than 12) are needed for in vitro testing for its biological activity.
5) The total extract may content polar, non-polar, waxy material like lipid, steroid, flavonoid etc.
6) The process is expensive and time consuming.
7) Yield is also lower than present invention.

OBJECTIVES OF THE INVENTION

An objective of the present invention is to provide an improved process for the extraction of organic compounds mahanine and mahanimbine useful for the treatment of cancer.

Another objective of the present invention is to provide pharmaceutical molecule mahanine useful for the treatment of glioma and cervical cancers.

Another objective of the present invention is to provide pharmaceutical molecule Mahanimbine (dehydroxy-mahanine), useful for inhibiting cell proliferation against seven different types of cancer (glioma, cervical carcinoma, lymphoid leukemia, myeloid leukemia, pancreatic cancer, colon cancer and lung cancer) in nineteen different cancer cell lines.

Yet another objective of the present invention is to identify the key functional group in mahanine and dehydroxy-mahanine and involvement of that group in cytotoxicity.

Yet another objective of the present invention is to provide cheaper and simpler isolation procedure of two pharmaceutical molecules mahanine and mahanimbine.

Yet another objective of the present invention is to establish the anti-cancer activity of EtOAc extract enriched in mahanine and mahanimbine against glioma and cervical cancer.

Yet another objective of the present invention is to make better yield of mahanimbine.

Yet another objective of the present invention is to provide the lower dose of cisplatin and paclitaxcel by using mahanine to reduce their cytotoxic effect.

Yet another objective of the present invention is to check that after coming in blood circulation whether mahanine can form secondary metabolites or not.

Previously our group has demonstrated that mahanine is a very potent anti-leukemic compound in vivo and in vitro with minimal toxicity towards BALB/c and NH(nu/nu) nude mice.

In another orthotopic immune deficient nude mouse model, the compound showed strong anticancer activity against pancreatic cancer. Both the Sub-Cutaneous and Orthotopic mouse model study strongly support the in vivo efficacy of mahanine against cancer cells.

On the other hand, Hsp90 is the hot target of chemotherapeutic drugs towards the cancer and a very few compounds were established to inhibit the chaperonic function of Hsp90 in malignant cells.

Yet the main drawbacks of the most of these compounds are formulation difficulties due to solubility problem, hepatotoxicity, in vivo variable pharmacokinetics and efflux by P-glycoprotein resulting into drug resistance.

Main objective of the present invention is to develop mahanine as a novel new generation herbal Hsp90 inhibitor by targeting most difficulty manageable cancer like glioma along with cervical cancer and poor prognostic pancreatic adenocarcinoma.

Another objective of the present invention is to identify some target of mahanine and some novel interactive cellular regulations through which it may transmit its apoptotic signal and triggered the programmed cell death.

Yet another objective of the present invention is to identify that is there any role of mahanine to disrupt the onco-chaperonic complex formation and thus by interfere with the function of Hsp90 because in cancer the expression of Hsp90 become high and it produce high level of oncogenic factors.

Yet another objective of the present invention is to identify whether mahanine can down-regulate the Hsp90 client protein status or not.

Yet another objective of the present invention is to recognize whether mahanine mediated Hsp90 client protein degradation is proteasome dependent or not.

Yet another objective of the present invention is to know the status of other co-chaperone of Hsp90 after mahanine treatment.

Yet another objective of the present invention is to recognize whether mahanine can inhibit chaperone co-chaperone complex formation.

Yet another objective of the present invention is to identify whether mahanine can obstruct ATP binding to Hsp90 or not.

Yet another objective of the present invention is to establish whether mahanine can directly bind to Hsp90 by Surface Plasmon Resonance (SPR) method.

Yet another objective of the present invention is to study drug-protein interaction molecular modeling approach.

Yet another objective of the present invention is to analyze the functional activity of the mahanine-treated pancreatic cancer cells.

Yet another objective of the present invention is to establish mahanine as a novel Hsp90 inhibitor by targeting most difficulty manageable cancer like glioma along with cervical cancer and poor prognostic pancreatic adenocarcinoma.

BRIEF DESCRIPTION OF THE FIGURES

The application file contains drawings executed in color (FIGS. 23 and 24). Copies of this patent or patent application with color drawings will be provided by the Office upon request and payment of the necessary fee.

FIG. 13 shows the concentration of mahanine and dehydroxy-mahanine determined in MeOH extract, EtOAc and purity of isolated mahanine and dehydroxy-mahanine from *Murraya koengii* leaf extract.

SUMMARY OF THE INVENTION

Figure 1:
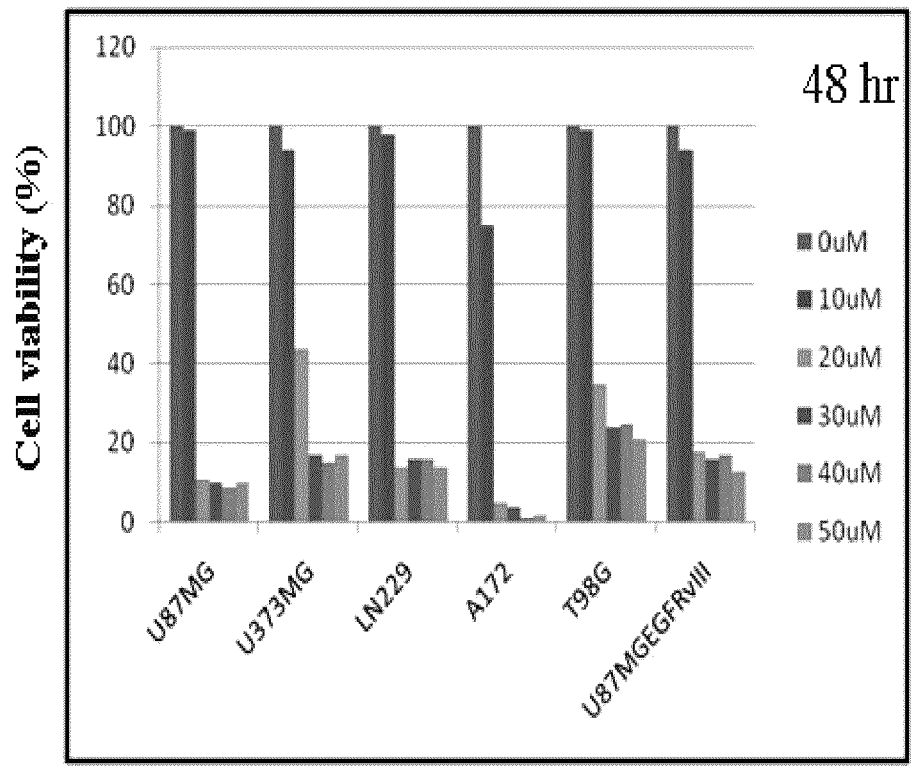
FIG. 1 shows Mahanine inhibited cell proliferation in glioma cells and $IC_{50}$ values against different cell lines.

Accordingly, present invention provides a process for the isolation of compound of general formula 1:

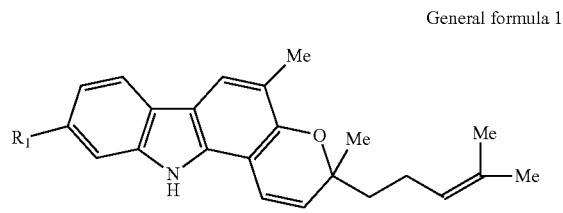

General formula 1 wherein $R_1$=H mahanimbine (1a) or $R_1$=OH mahanine (1b);

from the extract of *Murraya koeniigii* wherein the said process comprising the steps of:
  i. extracting leaves of *Murraya koeniigii* with methanol followed by concentrating to obtain residue;
  ii. dissolving the residue as obtained in step (i) in solvent followed by adding 8 to 10% acid (e.g., or 5% to 20% acid, such as 5% to 10%, 5% to 15%, 8% to 15%, and 8% to 20%);
  iii. separating the acid soluble part from the mixture as obtained in step (ii) and making the solution alkaline to obtain a precipitate;
  iv. dissolving the precipitate as obtained in step (iii) in ethyl acetate followed by evaporating to obtain an alkaloid; and
  v. subjecting the alkaloid as obtained in step (iv) to repeated (e.g., more than once, twice, three times, or more) chromatography on silica gel using petrol-chloroform solvent as eluent followed by crystallization on petrol to obtain the compound of general formula 1.

In an embodiment of the present invention, acid used is selected from the group consisting of HCl, $H_2SO_4$, $CH_3COOH$ or $HNO_3$.

In another embodiment of the present invention, yield of the compound is in the range of 10 to 40% of methanolic extract.

In yet another embodiment of the present invention, solvent used is selected from the group consisting of chloroform, diethylether or ethylacetate.

In yet another embodiment of the present invention, the invention features a pharmaceutical composition including an effective amount of at least one compound of general formula 1 optionally along with pharmaceutically acceptable additives:

General formula 1

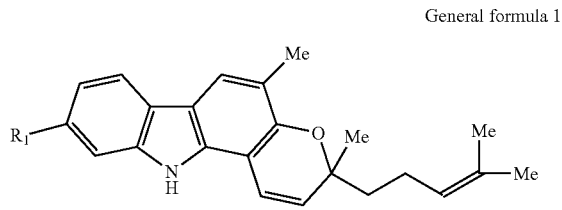

wherein $R_1$=H mahanimbine (1a) or $R_1$=OH mahanine (1b).

In yet another embodiment of the present invention, an effective amount of the compound of general formula 1 is in the range of 50-150 mg/kg body weight for 1 to 9 days.

In yet another embodiment of the present invention, compound 1a exhibits in vitro anticancer activity against human cancer cell lines selected from the group consisting of lymphoid cell lines, myeloid cell lines, glioma cell lines (U373MG, U87MG, LN229, T98G, A172), cervical cell lines (HeLa), pancreatic cell lines (Panc10.05, Panc1, AsPC1, MIAPaCa-2), colon cell lines and lung cancer cell lines (A549).

In yet another embodiment of the present invention, compound 1b exhibits in vitro anticancer activity against human cancer cell lines selected from glioma cancer cell line (U373MG, U87MG, LN229, T98G, A172) and cervical cancer cell line (HeLa).

In yet another embodiment of the present invention, compounds 1a and 1b inhibit cell proliferation in glioma and cervical cancer cells at $IC_{50}$ in the range of 10-20 μM and 30-50 μM respectively.

In yet another embodiment of the present invention, compound 1b hinders the Hsp90's chaperonic activity without hampering ATP binding site.

In an embodiment of the present invention, mahanine was derivatized to an epoxide form into the C20-C21 double bond. Mahanine was incubated with meta-chloro perbenzoic acid (MCPB) at room temp. for 48 hr and C20-C21 epoxy mahanine was generated. This epoxy mahanine was little less active than mahanine and $IC_{50}$ was identified in REH cell line was 18.4±1.1 μM after 48 hr treatment.

Yet another embodiment of the present invention provides a method for the treatment of cancer comprising administering to a patient suffering therefrom an effective dose of compound of general formula 1 or salt thereof, optionally along with pharmaceutically acceptable excipients.

Yet another embodiment of the present invention provides that the compound of general formula 1 is administrated by intra-peritoneal, oral, intra-muscular and sub-cutaneous routes.

Yet another embodiment of the present invention provides that the dosage of compound of general formula 1 for the treatment of cancer ranges between 50-150 mg/kg body weight for a period of 0 to 9 days.

Yet another embodiment of the present invention provides that the compound 1a is useful for the treatment of cancers selected from lymphoid leukemia, myeloid leukemia, gliomas, cervical carcinoma, pancreatic cancer, colon cancer and lung cancer.

Yet another embodiment of the present invention provides that the compound 1b is useful for the treatment of cancers selected from gliomas and cervical carcinoma.

Yet another embodiment of the present invention provides that the compound 1b hinders the Hsp90's chaperonic activity without hampering ATP binding site.

Yet another embodiment of the present invention provides that the compound of general formula 1 for use in treatment of cancers is obtained by chemical route or by herbal route.

For any of recited values herein, ±10% of that value are also included in any recited range.

DETAILED DESCRIPTION OF THE INVENTION

The present invention provides an improved process for isolation of mahanine and dehydroxy-mahanine showed better yield. The isolation procedure of mahanine and mahanimbine (dehydroxy-mahanine) are easier and cheaper than previously reported. The isolation procedure for mahanimbine is cheaper and yield is also higher than mahanine. The bioavailability results confirmed that the extract is enriched with mahanine and dehydroxy-mahanine in Murraya koenigii plant. Mahanine and dehydroxy-mahanine are isolated from an edible plant, so, it behaves like a nontoxic agent towards nonspecific tissues and body mass.

The present invention relates to purified herbal and nontoxic pharmaceutical molecules mahanine and mahanimbine, useful for the treatment various type of cancers. Both induced apoptosis and inhibited cell proliferation in cancer cell lines.

Mahanine induced higher mitochondria-mediated death cascade activation in T98G cells and HeLa cells as compared to other chemically modified compounds.

Mahanimbin (dehydroxy-mahanine) inhibited cell proliferation in all six glioma cells (U87MG, U373MG, LN229, A172 and T98G) and $IC_{50}$ values against different cell lines laid between 38-47 μM. Mahanimbin (dehydroxy-mahanine) induced higher mitochondria-mediated death cascade activation in T98G cells as compared to other chemically modified compounds. Mahanimbin (dehydroxy-mahanine) inhibited cell proliferation in cervical cancer cells (HeLa) and $IC_{50}$ being 36 μM. Mahanimbin (dehydroxy-mahanine) induced mitochondria-mediated death cascade activation in HeLa cells.

A comparative cytotoxicity study of mahanine and its analogs against glioma (T98G) and cervical (HeLa) cancer cells confirmed that both —OH group and —NH group are functionally active. O-methylated mahanine and N-methylated mahanimbine were inactive.

Approximately 2-2.5 fold less $IC_{50}$ exhibited by mahanine compared to mahanimbine against glioma (T98G) and cervical (HeLa) cancer cells suggested maximum contribution by —OH group compared to —NH group.

Comparative cytotoxicity study of mahanimbine and N-methylated mahanimbine against glioma (T98G) and cervical (HeLa) cancer cells confirmed that —NH group is also providing significant cytotoxic effect as N-methylated mahanimbine was inactive.

Normal cells [heart, liver, muscle and peripheral blood mononuclear cells (PBMC)] are less sensitive towards mahanine indicated by in vitro testing.

Vero cells (proliferating normal cells) are less sensitive towards mahanine indicated by in vitro testing.

in vivo toxicity testing indicates that mahanine is nontoxic towards nonspecific tissues and total body mass of normal Balb/c and athymic nude mice.

Mahanine potentiates paclitaxel-induced apoptosis in two cervical cancer (HeLa and ME180) cells. Mahanine potentiates cisplatin-induced apoptosis in HeLa cells. EtOAc extract was also potent to induce cell death in glioma (T98G) and cervical cancer (HeLa) and $IC_{50}$ being 140 and 134 μg/ml respectively.

Both mahanine and dehydroxy-mahanine are administrated through oral, intravenous, intramuscular or subcutaneous routes and intraperitonial routes.

Mahanine and dehydroxy-mahanine (mahanimbine) are easily absorbable components in blood circulation within 30 to 45 minutes of oral administration and identified as native mahanine and dehydroxy-mahanine by mass spectroscopy suggesting that no production of secondary metabolites making it an ideal molecule as anti-glioma and anti-cervical cancer.

Normal cells [heart, liver, muscle and peripheral blood mononuclear cells (PBMC)], vero cells (proliferating normal African monkey kidney cells) and WI-38 cells (proliferating normal human lung fibroblast cell line derived from embryonic lung tissue) are less sensitive towards mahanine indicated by in vitro testing.

C-3 hydroxyl group and NH group in the ring are two potential contributor for their cytotoxic effect.

O-methylated mahanine and N-methylated mahanimbine are more or less inactive with respect to native molecules.

Mahanine showed minimum toxic effects in vivo indicating that mahanine is nontoxic towards nonspecific tissues of athymic nude mice model.

In vivo testing of mahanine did not show any adverse change in total body mass of normal Balb/c and athymic nude mice model.

More particularly, present invention further relates to mahanine, a unique, non-toxic, carbazole alkaloid, directly binds to Hsp90 and thereby hinder the formation of chaperone-cochaperone superchaperonic complex by implanting itself into the Cdc-37 binding site of Hsp90 and responsible for successful apoptosis of cancer cells.

Table 1 represents $IC_{50}$ values against different cell lines for mahanine and mahanimbine.

TABLE 1

| Cancer Type | Subtype | Cell lines | Mahanine $IC_{50}$ (µM) at 48 hrs | Mahanimbine $IC_{50}$ (µM) at 48 hrs |
|---|---|---|---|---|
| Lymphocytic leukemia | T-Cell leukemia | Molt-3 | 10.6 ± 0.3 | 22.6 ± 0.6 |
| | | Molt-4 | 10.7 ± 0.6 | 28 ± 0.2 |
| | | CEM C7 | 10.2 ± 0.1 | 27.4 ± 0.3 |
| | B-cell leukemia | REH | 11.6 ± 0.7 | 24.3 ± 0.7 |
| Myelocytic leukemia | Chronic | K562 | 13.0 ± 1.1 | 25.1 ± 0.1 |
| Glioma | | U373MG | 16.8 ± 0.6 | 41.2 ± 0.25 |
| | | U87MG | 13.4 ± 0.4 | 42.6 ± 0.4 |
| | | LN229 | 13.7 ± 0.3 | 46.3 ± 0.1 |
| | | T98G | 16.1 ± 0.9 | 43.6 ± 0.2 |
| | | A172 | 11.6 ± 1.0 | 38.4 ± 0.8 |
| Pancreatic | | MIAPaCa-2 | 13.9 ± 0.9 | 35.2 ± 0.1 |
| | | AsPC1 | 17.2 ± 0.7 | 31.75 ± 0.2 |
| | | Panc1 | 16.5 ± 0.2 | 32.8 ± 0.1 |
| | | Panc10.05 | 18.5 ± 1.6 | 38.2 ± 0.1 |
| Lung | | A549 | 12.8 ± 1.1 | 37.0 ± 0.1 |
| | | NCIH23 | 7.08 ± 0.1 | 31.8 ± 0.2 |
| Colorectal | | HCT116 | 13.5 ± 0.8 | 33.5 ± 0.3 |
| | | SW480 | 16.0 ± 0.3 | 36.4 ± 0.5 |
| Cervical | | HeLa | 13.2 ± 1.1 | 34.8 ± 0.1 |
| Normal cell line | | Vero | >100 | >100 |
| | | WI-38 | >65 | — |

Although Mahanine showed anticancer activity against only nine cancer types like leukemia, lymphoma, colon, pancreatic, ovarian, prostate, epidermoid and breast and lung cancer, however its activity against many more cancer types are still not known. There is no report regarding its activity in glioblastoma and cervical carcinoma. Here we report the anti-cancer activity of mahanine from *Murraya koenigii* for the treatment in glioblastoma and cervical carcinoma. Additionally another new molecule mahanimbine (dehydroxy-mahanine) was isolated from the same plant and this molecule showed broad spectrum anti-cancer activity against seven different types of cancer (lymphoid leukemia, myeloid leukemia, glioma, cervical carcinoma, pancreatic cancer, colon cancer and lung cancer) being nontoxic towards normal cells. The isolation procedure for mahanimbine is cheaper and yield is also higher than mahanine. Both the compound induced apoptosis by activation of mitochondria-mediated death cascade both in glioma and cervical cancer cells. C-3 hydroxy group and NH group in the ring is two potential contributors for their cytotoxic effect. O-methylated mahanine and N-methylated mahanimbine are more or less inactive with respect to native molecules. Mahanine reduced the effective doses of cisplatin and paclitaxel in cervical cancer showing better efficacy and therefore can be used as an adjunct chemotherapeutic agent to reduce toxicity of known toxic anti-cancer drugs. Therefore, it was observed that mahanine proteolytically inhibited different client proteins of Hsp90. It was identified that mahanine inhibited the complex formation between Hsp90-Cdc37, by which it may act as a Hsp90 inhibitor. Moreover, mahanine could not obstruct ATP binding to the Hsp90.

The docking and simulation studies of mahanine with its target protein Hsp90 and have shown the structural mechanism of mahanine being a potential anti cancer target leading to apoptosis of cancer cells.

Mahanine treatment also enhances the intracellular $Ca^{2+}$ concentration and thus resulting into endoplasmic reticular stress. Additionally, this purified herbal compound can functionally inhibit the in vitro cell migration, colony formation and in vitro tubular differentiation. Therefore, mahanine, a purified carbazole alkaloid is a potent, novel Hsp90 inhibitor by disrupting Hsp90-Cdc37 complex formation.

More particularly, present invention further relates to mahanine as a potent Hsp90 inhibitor and to find whether mahanine can directly bind to the Hsp90 which is playing as an interactive part with the different onco-chaperonic complexes and proteins and thereby helping the cancer cells towards apoptosis. Additionally, the effect of pharmacological inhibition Hsp90 with other important cellular regulations is also identified.

Mahanine can hinder the Hsp90's chaperonic activity without hampering ATP binding site. Accordingly, mahanine should be considered as a unique Hsp90 inhibitor wherein Cdc-37 binding interface is involved therefore expected to become less toxic to the normal cells unlike other reported Hsp90 inhibitor (17-AAG) which can bind ATP binding site, hence more toxic.

Moreover, mahanine and dehydroxy-mahanine are easily absorbable components in blood circulation within 30 minutes of oral administration and identified as native mahanine and dehydroxy-mahanine by mass spectroscopy suggesting that no production of secondary metabolites making it an ideal molecule as anti-glioma and anti-cervical cancer agents.

Here glioma, cervical cancer and pancreatic adenocarcinoma for the establishment of activity of this herbal remedy by targeting Hsp90 specific cellular protein to inhibit broad-spectrum cellular onco-proteins like Akt, B-Raf, Stat-3, Bcl-$X_L$ etc towards those cancer types are used. To face a typical problem of drug resistant, so, for that we desperately need new subset of drugs or one thrilling drug, which can inhibit broad-spectrum survival pathways and activate different apoptosis inducing factors or proteins.

Mahanine overcome EGFR mutation which is the most lethal in glioma. Mahanine is Hsp90 inhibitor in epithelial carcinoma like glioblastoma, cervical carcinoma and adenocarcinoma cells. Mahanine reduced the effective doses of cisplatin and paclitaxel in cervical cancer showing better efficacy of these two known highly cytotoxic drugs. Mahanine can be used as an adjunct chemotherapeutic agent to reduce toxicity of known toxic anti-cancer drugs. EtOAc extract enriched in mahanine and dehydroxy-mahanine was also potent to induce cell death in glioma and cervical cancer and $IC_{50}$ being 140±10 and 134±15 µg/ml respectively. Mahanine also induces endoplasmic reticulum stress in pancreatic cancer suggesting possibility of new target identification. Mahanine inhibits pancreatic adenocarcinoma cells chemo-migration, cell haptotaxis and colony formation useful as anti-metastatic agent. Mahanine also induces the differentiation of poorly differentiated pancreatic carcinoma cells.

Figure 2:
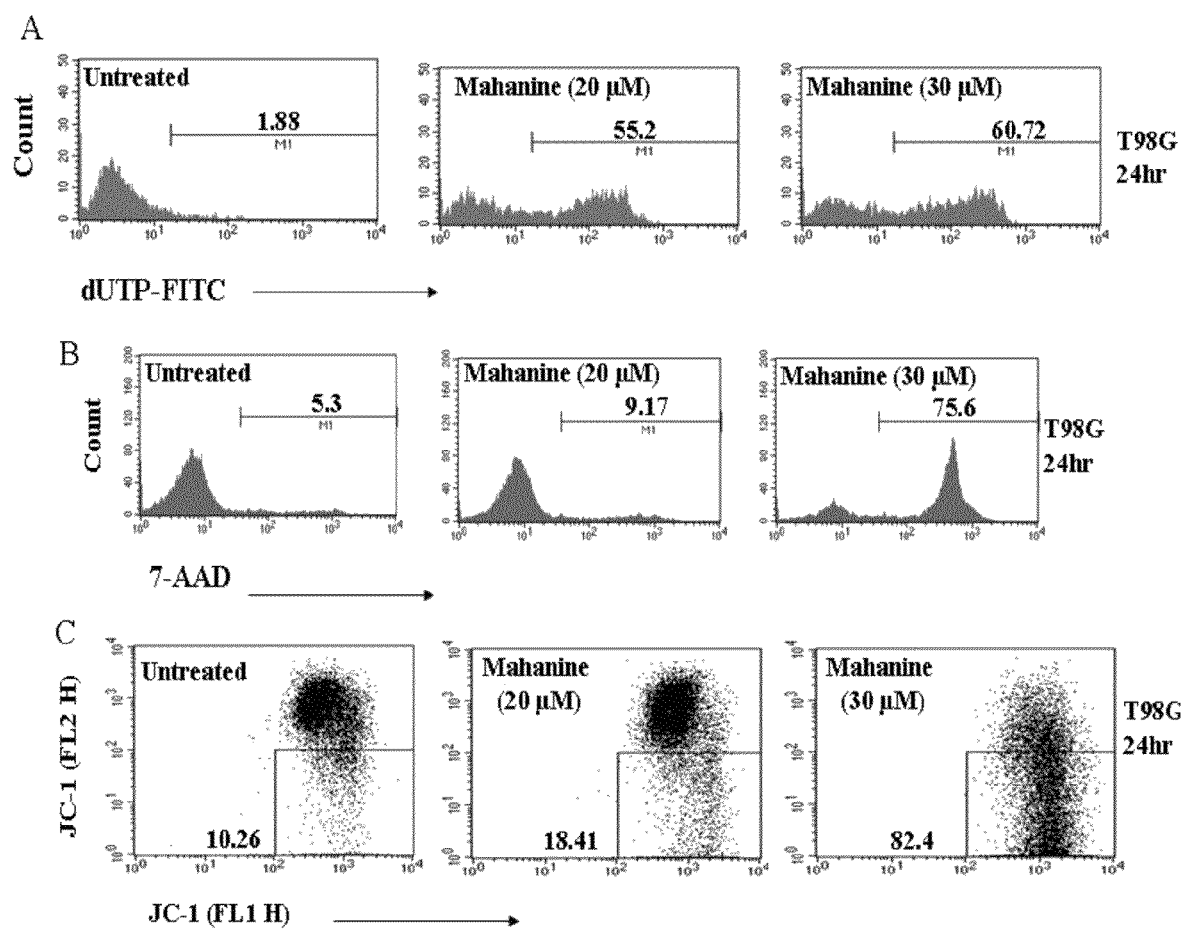
FIG. 2 shows Mahanine induced apoptosis in glioma cells measured by TUNEL (a), 7-AAD positively (b) and JC-1 staining assay (c).

Mahanine is a Potential Apoptosis Inducer in Glioblastoma Even in Grade IV Stage and Also Overcome the Mutation Barrier Mahanine may be useful for the regression of different glioblastoma cell lines (U87MG, U373MG, LN229, A172 and T98G), where the $IC_{50}$ values are between 12-17 µM after 48 hr (FIG. 1). Cell death is confirmed by 7-AAD positively after mahanine treatment by flow cytometric analysis. Mitochondrial involvement is also confirmed by in cell death in glioblastoma cell lines induced by mahanine after JC-1 staining assay. DNA fragmentation detection by TUNEL assay proved further that mahanine induced cell death is an apoptosis (FIG. 2).

If we want to project this compound as a potential therapeutics of brain tumour, it should overcome the barrier of most oncogenic and lethal mutation of EGFR that is documented as EGFRvIII. To answer this question, we selected the cell line over expressing EGFRvIII (U87MGEGFRvIII) and we identified that particular modified cell line has the $IC_{50}$ value around 14 µM after 48 hrs treatment of mahanine (FIG. 1). From here we can confirmed that EGFRvIII is not inhibiting the effect of mahanine, so it can be a useful drug for those patients who are carrying this lethal mutation.

Figure 3:
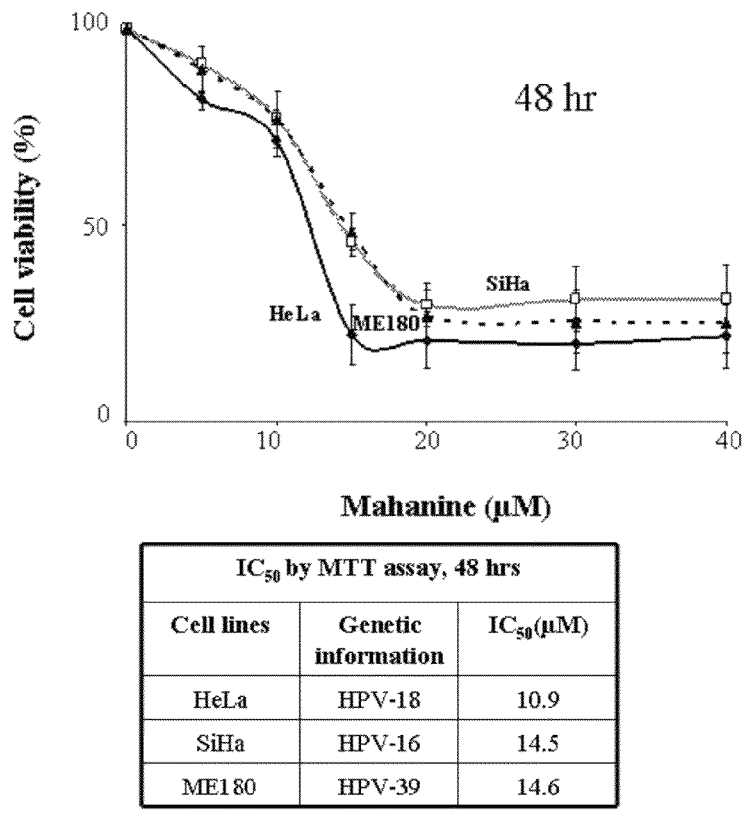
FIG. 3 shows Mahanine inhibited cell proliferation in cervical cancer cells and $IC_{50}$ values against different cell lines.

Mahanine Inhibited Cell Proliferation in Cervical Cancer Cells and Induces Apoptosis In order to investigate whether mahanine can induce growth inhibition in cervical cancer cells, HeLa, SiHa and ME180 cells were treated with mahanine with the increasing concentrations (0-40 µM) for 48 hr (FIG. 3). Mahanine was found to exhibit anti-proliferative effect on the three cervical carcinoma cell lines in dose-dependent manner as detected by MTT assay. $IC_{50}$ values of mahanine on HeLa, SiHa and ME180 cells were 10.9 µM, 14.5 µM and 14.6 µM respectively after 48 hr.

To confirm mahanine-induced anti-proliferative activity was due to apoptosis, we treated HeLa, SiHa and ME180 cells with 25 µM of mahanine, stained with 7-AAD and then analyzed by flow cytometry. We observed that presence of mahanine resulted in 92.28%, 97.13% and 80.5% apoptosis in HeLa, SiHa and ME180 cells respectively. This increasing percentage of 7-AAD+ve cells clearly dictates mahanine-induced cell death of cervical cancer cells (FIG. 4A).

Figure 4:
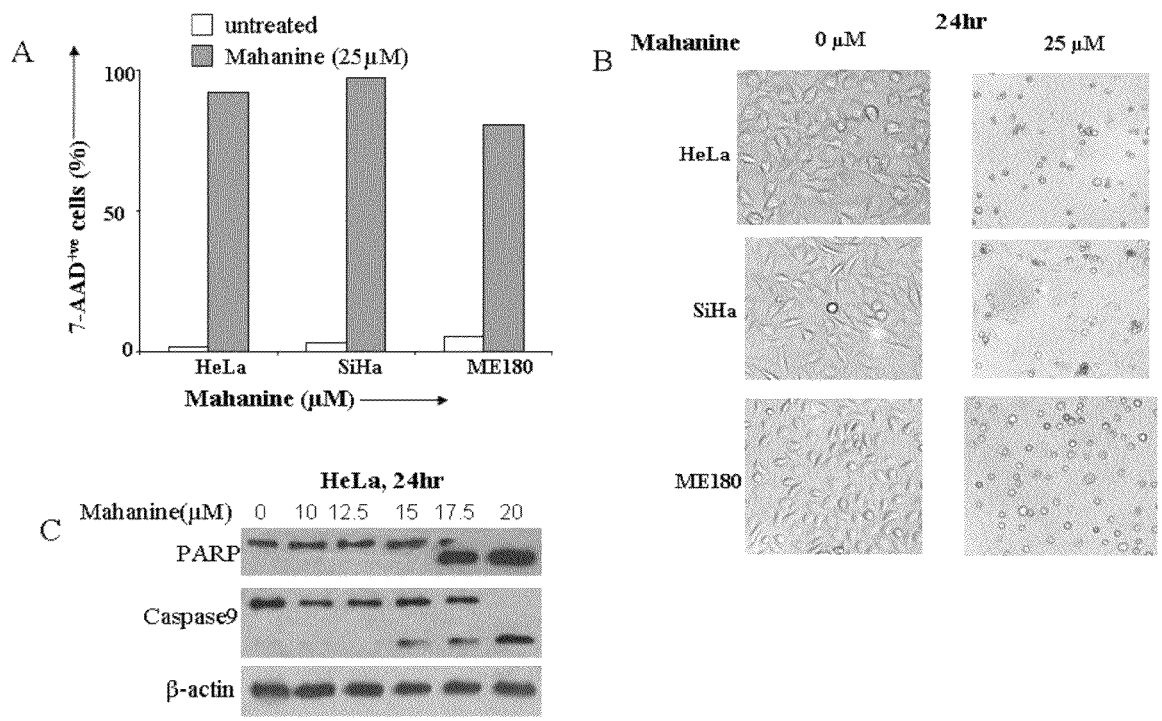
FIG. 4 shows that Mahanine induces apoptosis in cervical cancer cells (a-c).

Microscopic study showed that presence of mahanine caused cell shrinkage, membrane blebbing and nuclear condensation (FIG. 4B). The apoptosis induced by mahanine was further confirmed by detecting poly (ADP-ribose) polymerase cleavage and caspase activation, the two executioners of apoptosis. Exposure of mahanine to HeLa cells led to evident cleavage of poly (ADP-ribose) polymerase and caspase-9 in dose-dependent manner (FIG. 4C). Together, these results demonstrate that mahanine-induced cytotoxicity is mainly through apoptotic pathway.

Figure 5:
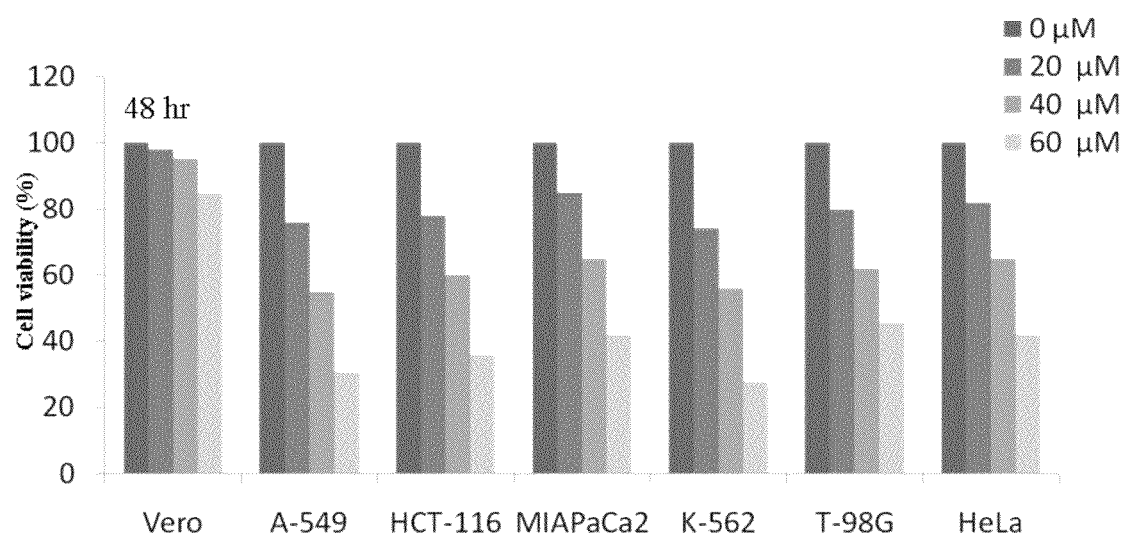
FIG. 5 shows Dehydroxy-mahanine as a potential molecule to reduce cancer cell proliferation in various cancer types.

Dehydroxy-Mahanine was Also a Potential Molecule to Reduce Cancer Cell Proliferation in Various Cancer Types Mahanimbine (dehydroxy-mahanine), a natural derivative of mahanine was an active molecule against different cell lines of different cancer types and showed significant dose dependent cell death after 48 hr of treatment (FIG. 5). This compound showed a wide range of $IC_{50}$ value from 20-45 µM after 48 hr treatment by MTT assay (FIG. 5). All the cancer types (leukemia, glioma, cervical, pancreatic, colon and lung cancer) used against dehydroxy-mahanine were potentially inhibited. So, we could use dehydroxy-mahanine also as a chemotherapeutic agent. But both mahanine and mahanimbine in combination did not show any significant additional effect in the tested cancer cell lines.

—OH is Identified as the Main Functional Group Responsible for the Cytotoxicity

Figure 6:
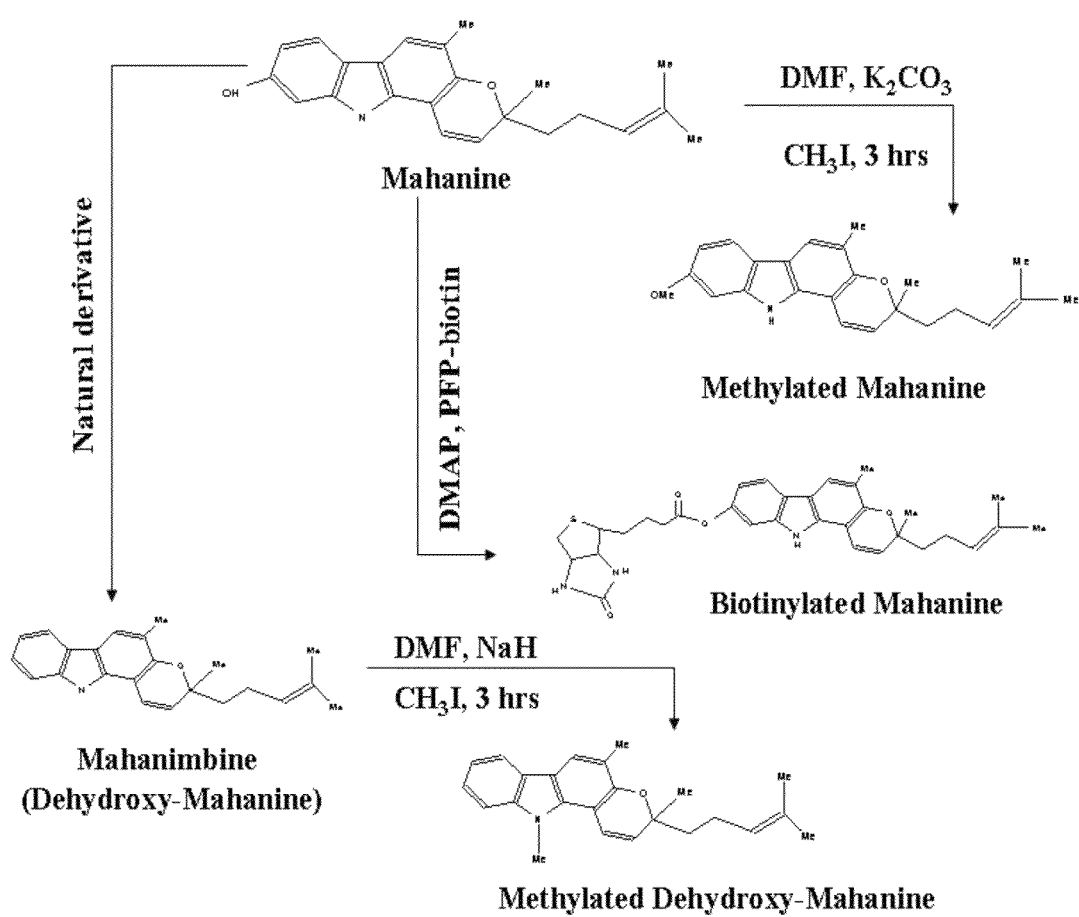
FIG. 6 shows a preparation of chemically modified derivatives of mahanine and dehydroxy-mahanine.
Figure 7:
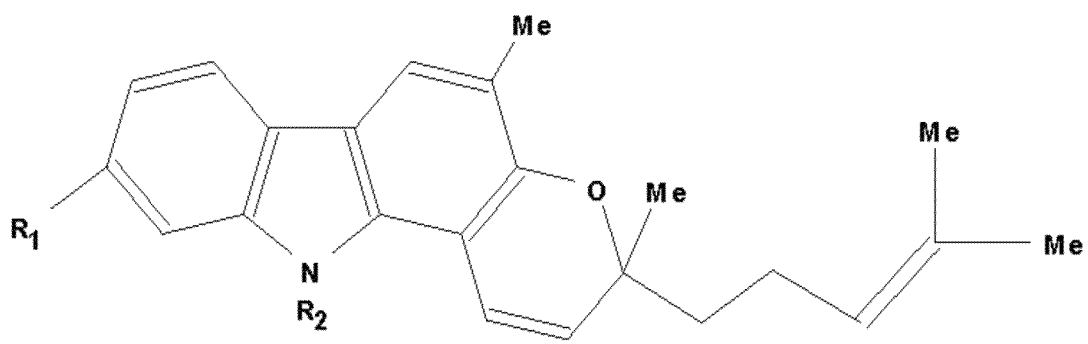
FIG. 7 shows structures of mahanine and its analogs.
Figures 8, 9:
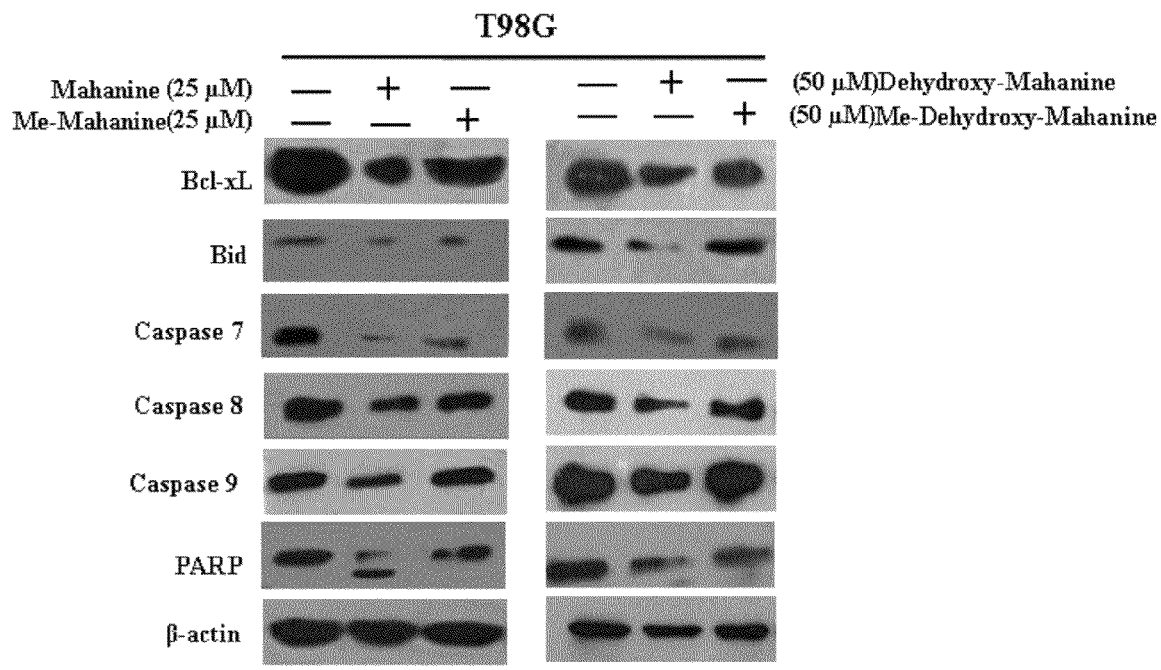
FIG. 8 shows comparative cytotoxicity testing of mahanine and its analogs by MTT assay in glioma and cervical cancer cells.
FIG. 9 shows Mahanine induced mitochondria-mediated death cascade activation in T98G and HeLa cells as compared to other chemically modified compounds.

We also aimed to study the active functional groups of mahanine purified from leaves of *Murraya koenigii*. Accordingly, functional groups like —OH group at C3 and NH group of mahanine has been chemically modified (FIGS. 6 and 7). Here we confirmed the dose dependent anti-proliferative activity of mahanine and its four derivatives in HeLa and T98G cell lines from two different types of cancers. Mahanine showed optimum activity as compared to all four derivatives with minimal effect on Vero cells identified by cell viability testing by MTT assay (FIG. 8). Mahanine is found to be the best mitochondrial membrane depolarizer in both the cell lines. A significant drop in BclxL, Bid, caspase-7, caspase-8 caspase-9 and cleavage of PARD in mahanine-treated T98G and HeLa cells compared to methylated mahanine treatment confirm the essential role of —OH group (FIG. 9). Similar observations in mahanimbine and N-methylated mahanimbine-treated cells, at higher doses, suggested some contribution of —NH group present in mahanine.

Here in this study we want to establish that mahanine and mahanimbine (dehydroxy-mahanine) are potential anticancer agents, accordingly we selected glioma and cervical carcinoma cancer types and different cell lines in a particular cancer documented in. So, here we identified that mahanine is the more potent anti cancer agent over dehydroxy-mahanine.

Figure 10:
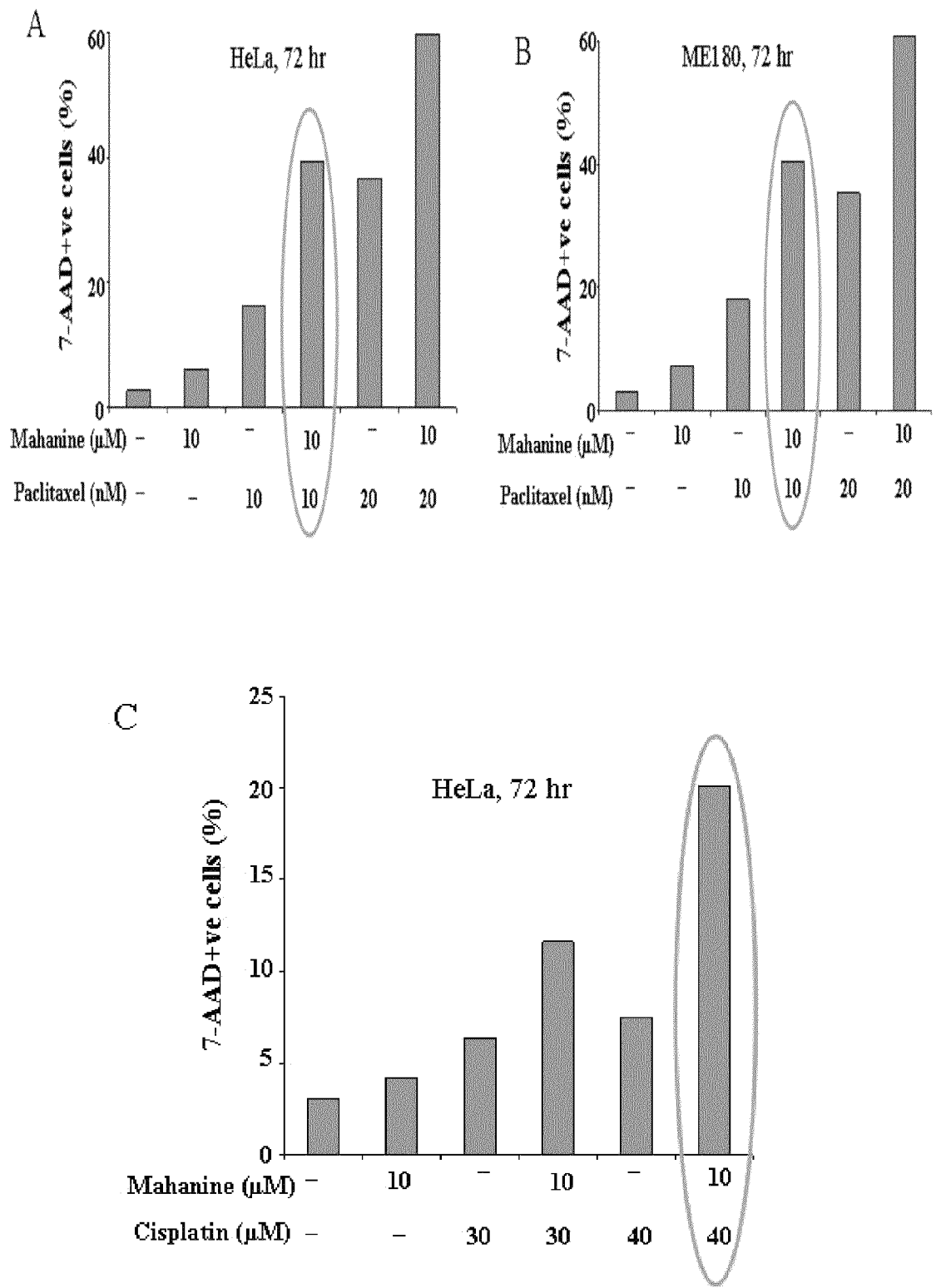
FIG. 10 shows that Mahanine potentiates paclitaxel-induced apoptosis in HeLa (a) and ME180 (b) cells and cisplatin induced apoptosis in HeLa (c) cells.

Mahanine Potentiates HeLa and ME180 Cells to Apoptosis by Paclitaxel and Cisplatin We investigated degree of apoptosis by 7-Aminoactinomycin D (7-AAD) staining. We observed apoptosis in cervical cancer cells after treatment with mahanine (10 µM), paclitaxel (10 µM and 20 µM) or cisplatin (30 µM and 40 µM) alone. However, in HeLa and ME180 cells, mahanine in combination with paclitaxel induced more apoptotic cell death in relative to single agent. Paclitaxel (10 µM) alone resulted in 16.19% and 18.21% apoptois in HeLa and ME180 cells respectively (FIGS. 10A and 10B). Combination treatment increased 7-AAD+ve cells by ~2.43 fold in comparison to paclitaxel alone. Cisplatin (40 µM) alone treatment caused ~7% of apoptosis in HeLa cells whereas; mahanine (10 µM) in combination with cisplatin (40 µM) increased apoptosis by ~2.56 fold (FIG. 10C).

Figure 11:
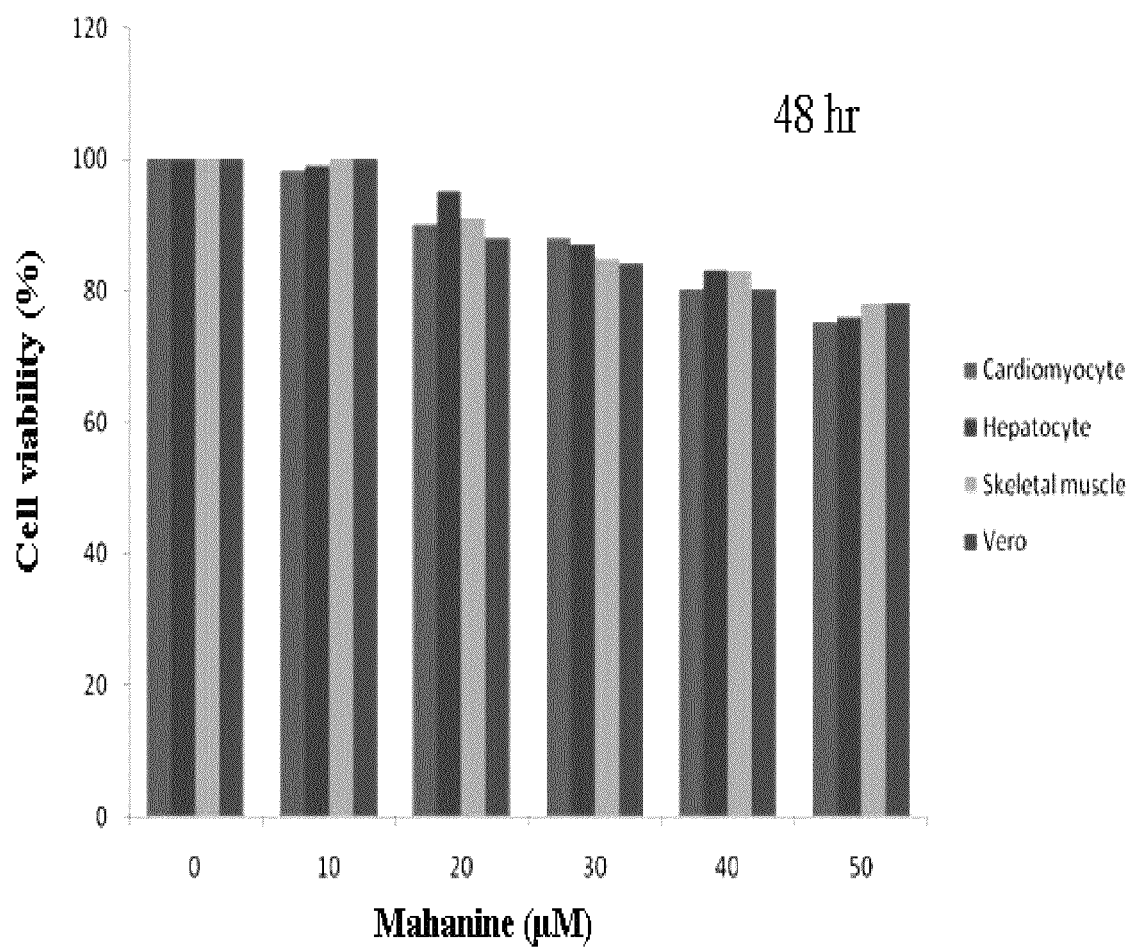
FIG. 11 shows less sensitivity of normal cells towards mahanine.
Figure 12:
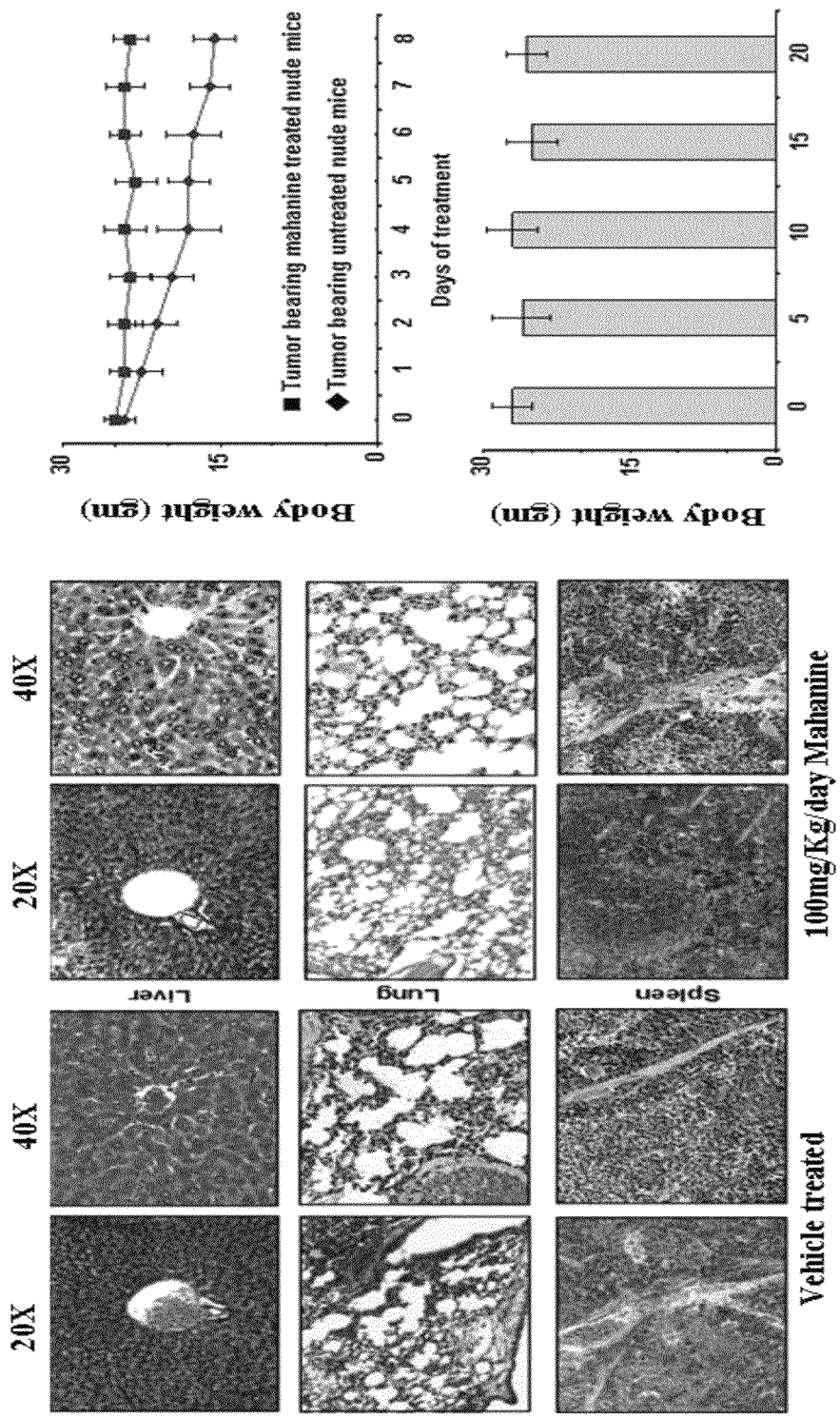
FIG. 12 shows in vivo toxicity testing indicating that mahanine is nontoxic towards nonspecific tissues and total body mass.

Mahanine is Easily Absorbable in Blood Stream and Non-toxic Towards Different Normal Cells and Non Specific Tissues Mahanine showed non-toxicity towards different normal cells isolated from different rat tissue and normal proliferating cell line Vero and WI-38 (normal lung fibroblast). Mahanine at 50 µM inhibited only 15-20% of normal cells (FIG. 11) where as mahanine at 20 µM inhibited almost 75-85% cancer cells. So, mahanine was a non-toxic agent in vitro condition. Mahanine also showed minimal toxicity in vivo condition also. In K562 xenograft bearing nude mice mahanine showed no toxic effect towards different nonspecific tissues like lung, liver and spleen. The adverse effect of mahanine towards body mass was also minimal and normal Balb/c mice could tolerate 150 mg/kg/day (1.5 fold over optimum dose) of mahanine for consecutive 20 days (FIG. 12).

Figure 14:
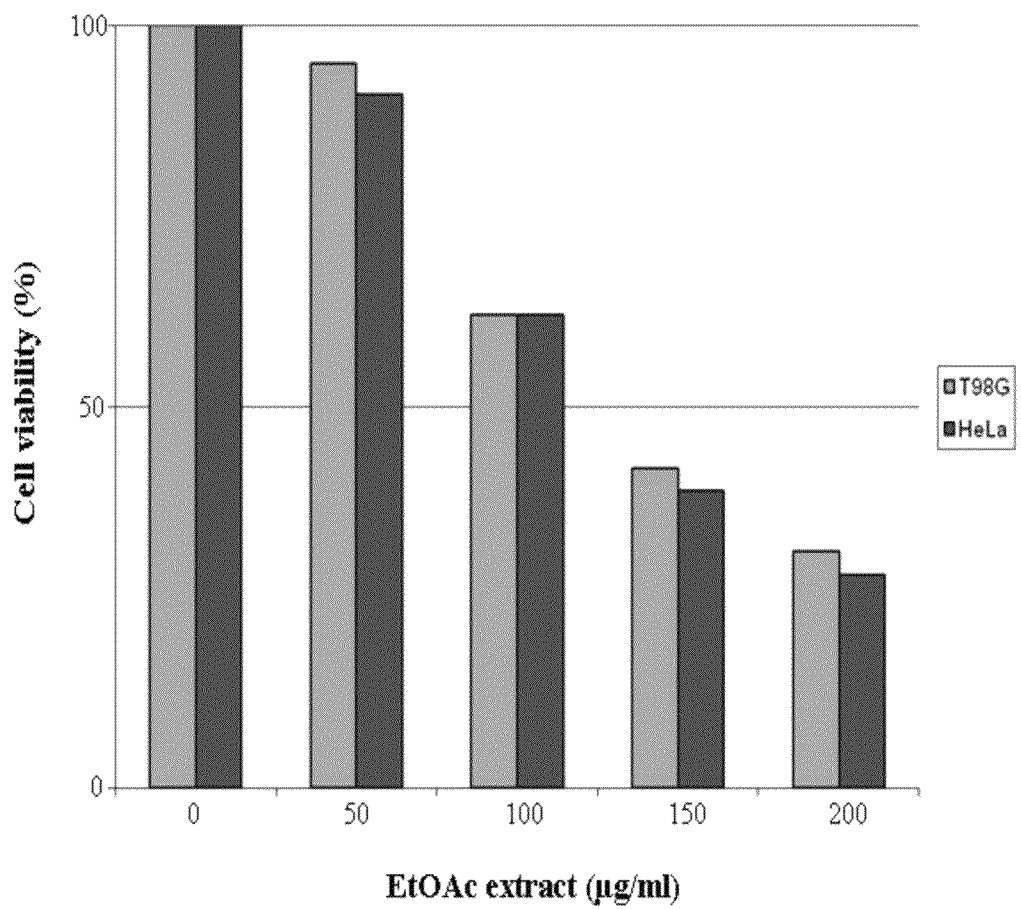
FIG. 14 shows that an EtOAc extract mediated cell death in Glioma (T98G) and cervical cancer (HeLa) cells.
Figure 15:
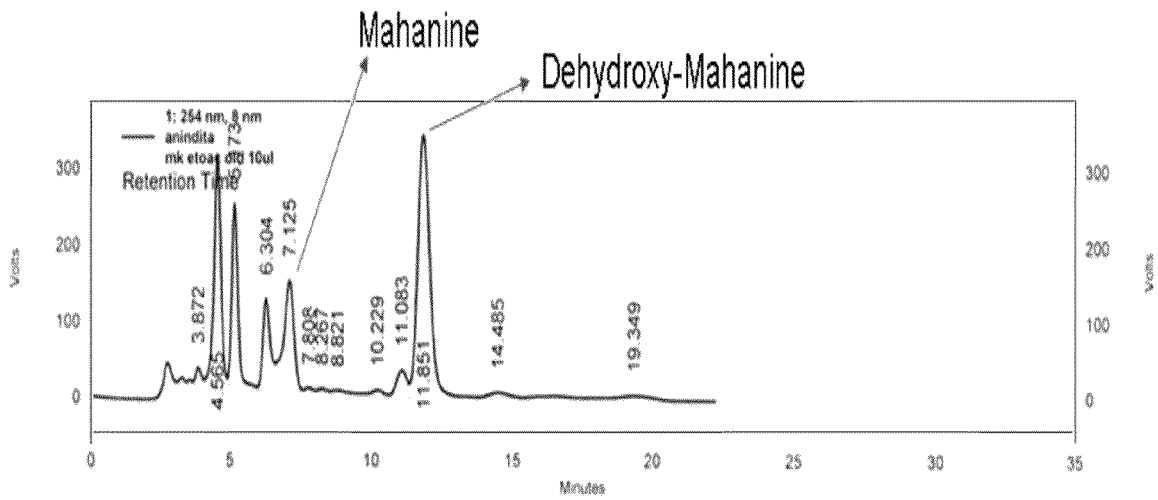
FIG. 15 shows that Mahanine and dehydroxy-mahanine are easily absorbable components in blood circulation.

EtOAc fraction of *Murraya koengii* leaf extract was enriched fraction of mahanine and mahanimbine (dehydroxy-mahanine) (FIG. 13) and after oral feeding in Balb/c mice with in 30 min both the compounds were available in blood serum identified by HPLC analysis (FIG. 15). So, we could use EtOAc extract as a chemotherapeutic combination because both mahanine and dehydroxy-mahanine were active against different cancer type because EtOAc extract was also potent to induce cell death in glioma (T98G) and cervical cancer (HeLa) and $IC_{50}$ being 140±10 and 134±15 µg/ml respectively (FIG. 14).

Mahanine Inhibited Cell Proliferation in Pancreatic Adenocarcinoma

Figure 16:
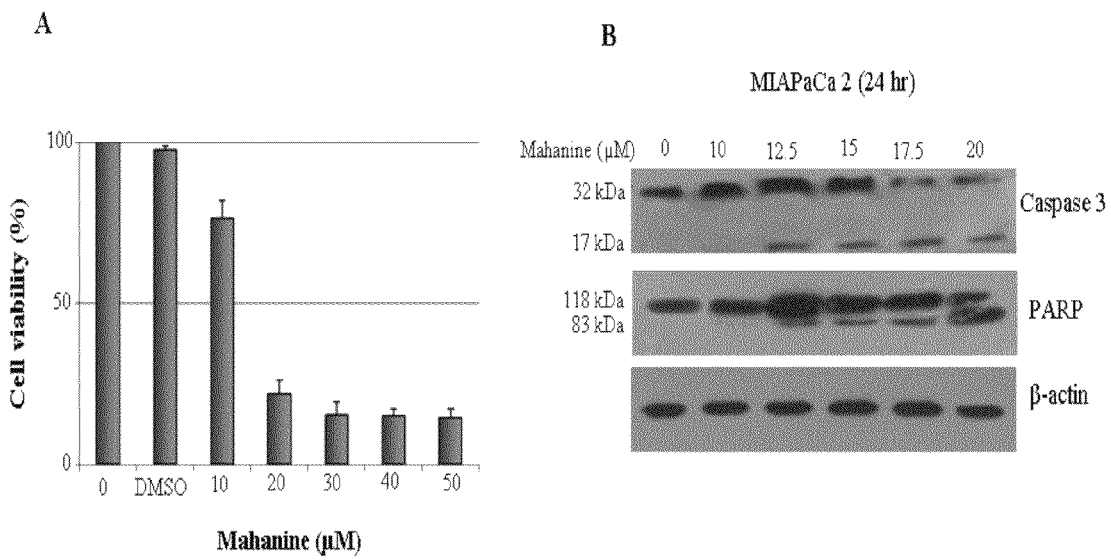
FIG. 16 shows Mahanine induced cell death in MIAPaCa-2 is apoptosis by activation of caspase and cleavage of PARD (a-b).

In order to investigate whether mahanine can induce growth inhibition in pancreatic adenocarcinoma, MIAPaCa 2, was treated with mahanine with the increasing concentrations (0-50 µM) for 48 hr (FIG. 16A). Mahanine was found to exhibit anti-proliferative effect on MIAPaCa-2 in dose-dependent manner as detected by MTT assay. $IC_{50}$ value of mahanine MIAPaCa2 cell was 13.9 µM after 48 hr (FIG. 16A). No inhibition in the cell proliferation was observed in solvent control.

Mahanine Induced Programmed Cell Death Revealed by Activation of Apoptotic Factors As the model cancer cells, here we take pancreatic cancer primary cell line MIAPaCa2. From the Western blot analysis we established that mahanine triggered the mitochondrial apoptosis as 24 hr incubation of mahanine (0-20 µM) triggered Caspase 3 activity and PARP cleavage (FIG. 16B).

Mahanine Mediated Degradation of Hsp90 Client Proteins

Figure 17:
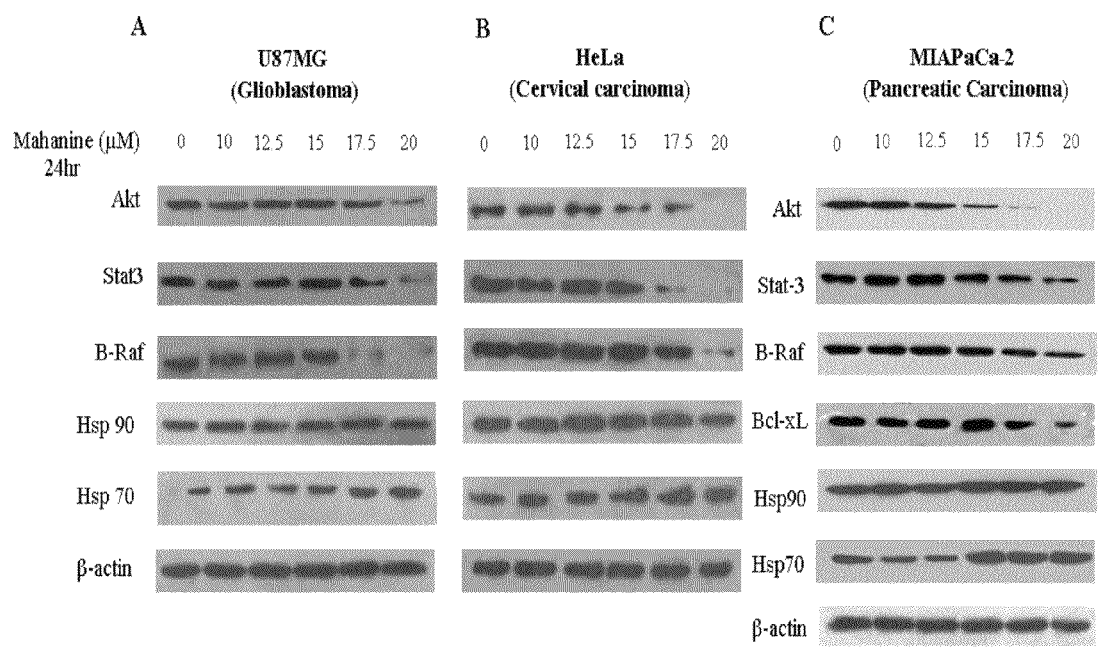
FIG. 17 shows that Mahanine induces Hsp90 client protein degradation in dose dependent manner with the up-regulation of Hsp70 and apparently unaltered protein expression of Hsp90 in U87MG (a), HeLa (b) and MIAPaCa 2 (c) cell lines at 24 hrs.

As Hsp90 is a major onco-chaperonic protein, we want to see whether mahanine can interact with Hsp90 and distort its functionality. To fulfill this aim first we want to identify the expression level of well-known Hsp90 client proteins. We observed that dose dependent downregulation of Akt, Stat-3, B-Raf in glioblastoma (FIG. 17A), cervical cancer (FIG. 17B) and Bcl-xL along with above mentioned client proteins were decreased in pancreatic cancer cell line also (FIG. 17C). Akt is more susceptible to mahanine treatment in both cervical and pancreatic cancer cell lines. 15 µM dose is enough to start the significant downregulation of Akt level in these two cell lines. Level of Hsp90 protein expression was maintained throughout the treatment where as Hsp70, another chaperone protein level was increased with mahanine treatment, which is a hallmark feature of Hsp90 inhibition (FIG. 17 A, B, C).

Hsp90 Client Protein Degradation was Proteosome Dependent

Figure 18:
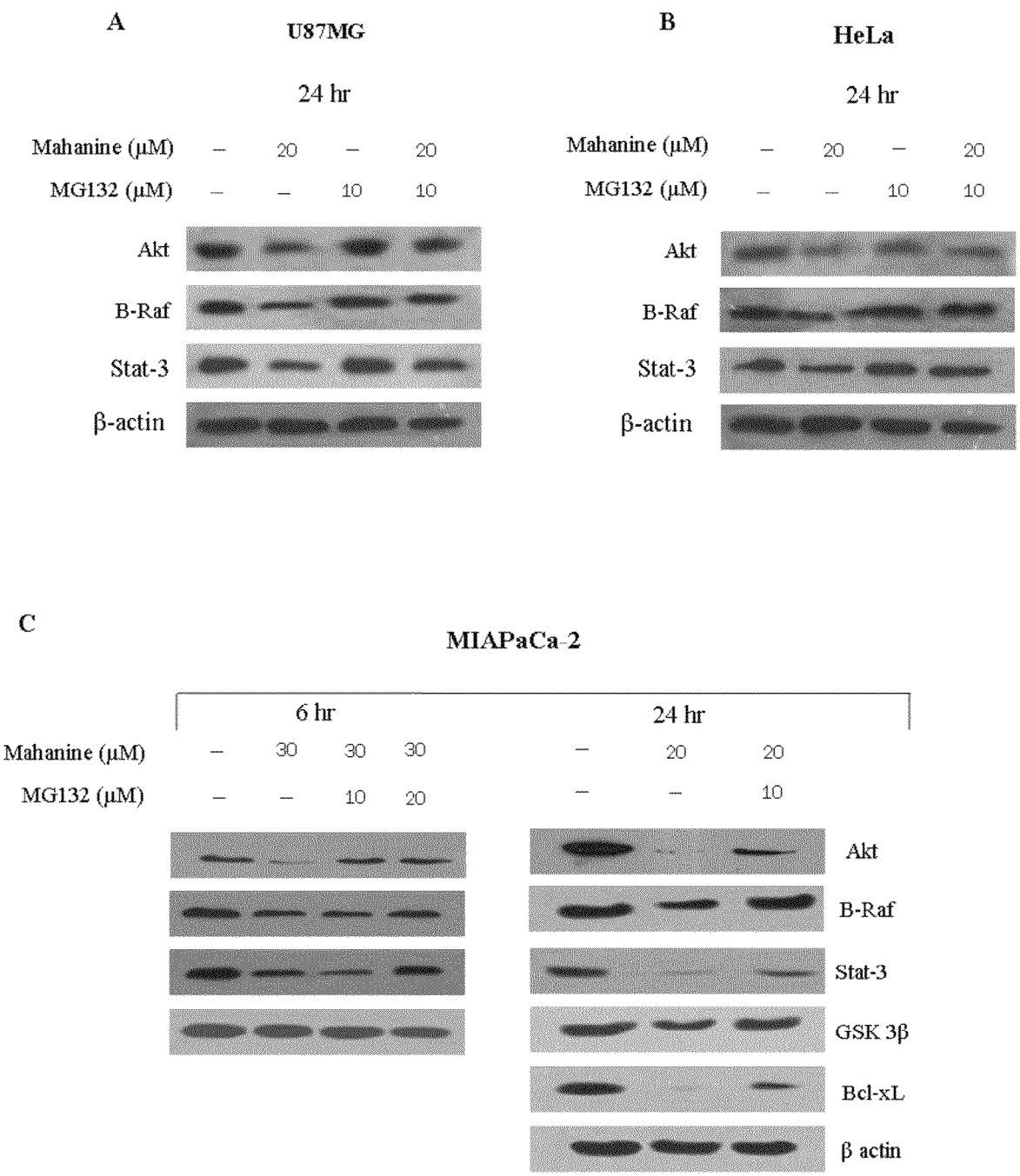
FIG. 18 shows Mahanine mediated Hsp90 client protein degradation through proteasome. 1 hr pretreatment of 10 µM MG132 can restore the client proteins in U87MG and HeLa after 24 hr mahanine treatment (a, b). The treatment with 30 µM and 20 µM dose of mahanine could be overcome by the pre-incubation of MIAPaCa 2 cells with 20 µM and 10 µM of MG132 for 6 hr and 24 hr respectively (c).

Next we want to address whether this client protein degradation is proteasome dependent or not. We identified that a 26S proteosomal inhibitor MG132 pre-treatment can restore the mahanine mediated client protein degradation. 10 µM pre incubation of MG132 was standardized to restore the well characterized client proteins status, i.e. Akt, Stat-3 and B-Raf, sufficiently after 24 hr mahanine treatment in U87MG (FIG. 18A), HeLa (FIG. 18B) along with GSK3β and Bcl-$X_L$ in pancreatic carcinoma cells (FIG. 18C). However, prior treatment with 20 µM MG132 also can restore mahanine mediated client protein degradation within the 6 hr (FIG. 18C). So, from here we confirmed that the decrease of client proteins is mediated by proteasome.

Mahanine Mediated Differential Regulation of Co-Chaperones Status

Figure 19:
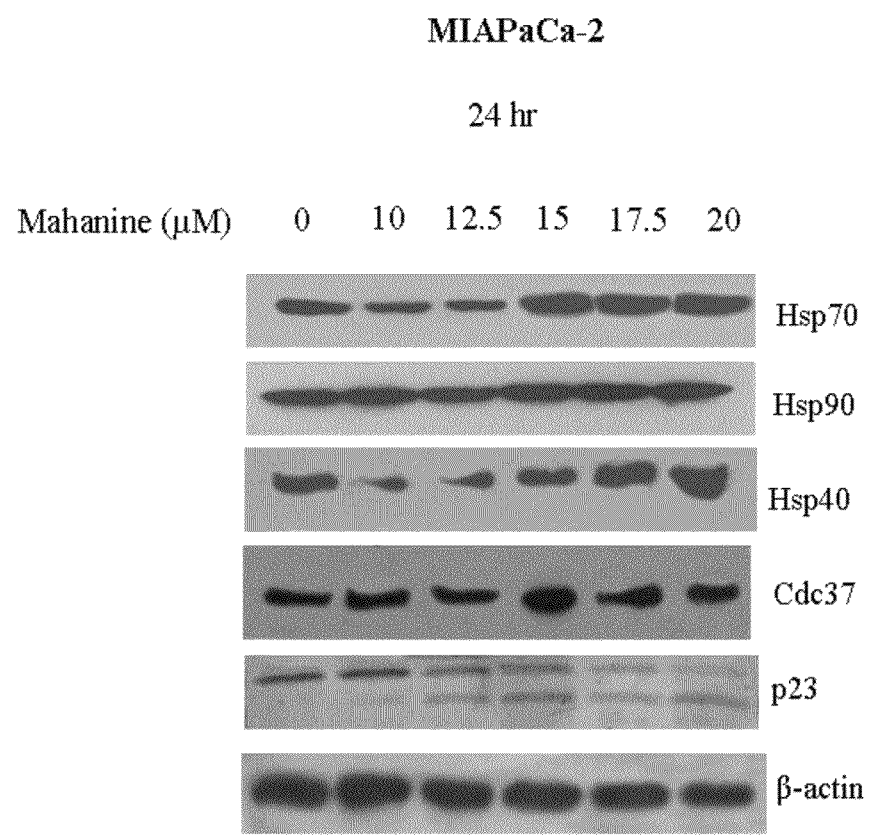
FIG. 19 shows the status of co-chaperones of Hsp90 in mahanine treated MIAPaCa 2 cell line after 24 hrs.

Our next aim to identify the status of several co-chaperones status in mahanine treated cells. To answer this question, we incubated MIAPaCa 2 cells in varying concentrations (0-20 µM) of mahanine for 24 hr. As the expression level of Hsp90 was maintained throughout the treatment, however, the Hsp70 expression level was increased in dose dependent manner, which is a hallmark feature of the functional inhibition of Hsp90. The intensity of Hsp40 protein level was also amplified, probably to aid the Hsp70. However, two other co-chaperones, Cdc37 and p23, also retained there protein expression level all through the treatment (FIG. 19).

Mahanine Induced Disruption of Complex Formation Between Hsp90-Cdc37

Till now we get some features from which we may conclude that mahanine may has an ability to inhibit Hsp90. But how does mahanine inhibit the Hsp90 function? To address this question we did immunoprecipitation assay to identify the association between Hsp90 with Cdc37, Hop and p23 separately.

In glioblastoma cell lines, U87MG, whole cell protein co-immunoprecipitation with Cdc37 showed dose dependent decrease of Hsp90 when blotted against anti Hsp90 antibody. Mahanine treated cells with 15 µM dose for 24 hr showed significant decrease of association of Hsp90-Cdc37 complex (FIG. 20A).

Figure 20:
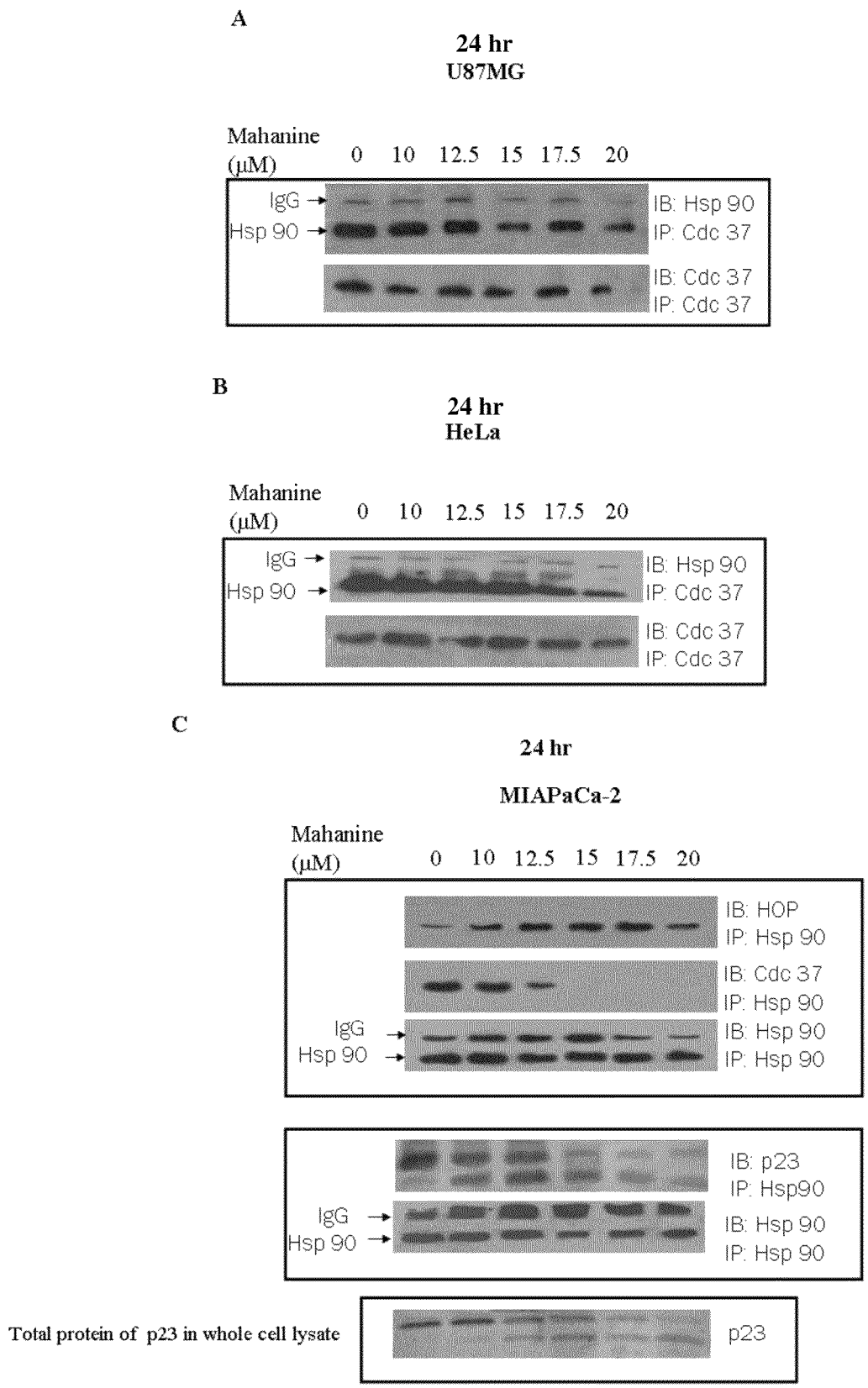
FIG. 20 shows that Mahanine disrupts the Hsp90-Cdc-37 chaperones complex. Dose dependent degradation of Hsp90-Cdc37 protein complex in U87MG and HeLa after 24 hr of mahanine incubation (a, b). Mahanine also degrades, as a result of dose responsiveness, Hsp90-Cdc37 chaperone-co-chaperone complex in MIAPaCa 2 after 24 hr, whereas no dissociation were observed in HOP and p23 (c).

Similarly, in cervical cancer cell line, HeLa, 17.5 µM dose was needed to initiate the dissociation of Hsp90-Cdc37 in this cell line (FIG. 20B).

On the other hand, in pancreatic cancer cell line, MIAPaCa2, Hsp90 mediated co-immune precipitation of Cdc37 showed also very similar data, where as Hop and p23 did not showed any dose dependent significant dissociation with Hsp90. In this cell line 12.5 µM dose was adequate to begin this protein-protein dissociation (FIG. 20C). Here, we identified that mahanine triggers the dose dependent inhibition of association between Hsp90 and Cdc37. By this mechanism mahanine inhibits the chaperonic functions of Hsp90, which trigger the misfolded client proteins to channelize them into degradation through proteasomal pathway.

Mahanine does not Affect the ATP Binding to Hsp90

Figure 21:
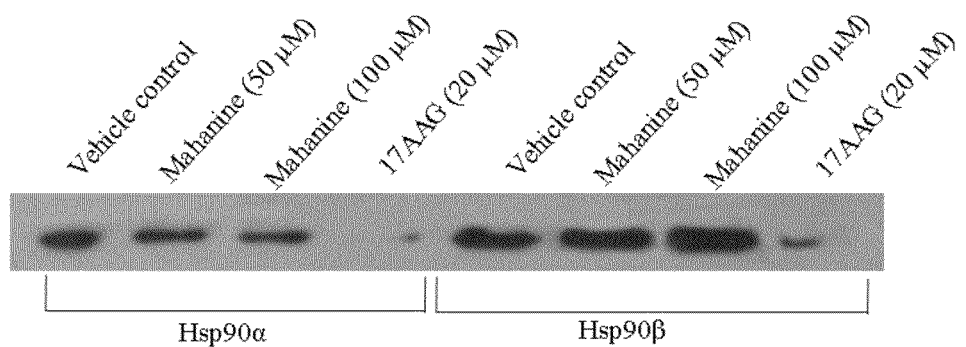
FIG. 21 shows that ATP binding of Hsp90 also did not obstructed by mahanine induction. A γ-ATP sepharose binding assay revealed that enhancement of successive dose of mahanine could not hamper the ATP binding onto purified Hsp90α and Hsp90β, whilst 17AAG blocked the same.

In order to address the question whether mahanine can obstruct the ATP binding site of Hsp90, we performed an ATP binding assay. To carry out this experiment, both the isoforms of Hsp90, Hsp90α and Hsp90β were used. The two doses of mahanine, 50 and 100 µM could not reduce the ATP binding pattern to the purified Hsp90s. On the other side, to pursue the positive control of the assay, a well known Hsp90 inhibitor, 17AAG easily hindered the ATP binding to both of the isoforms of purified Hsp90s where as vehicle control did not interfere with the Hsp90-ATP binding (FIG. 21).

Biophysical Analysis of Specific Binding of Mahanine Towards Hsp90

Figure 22:
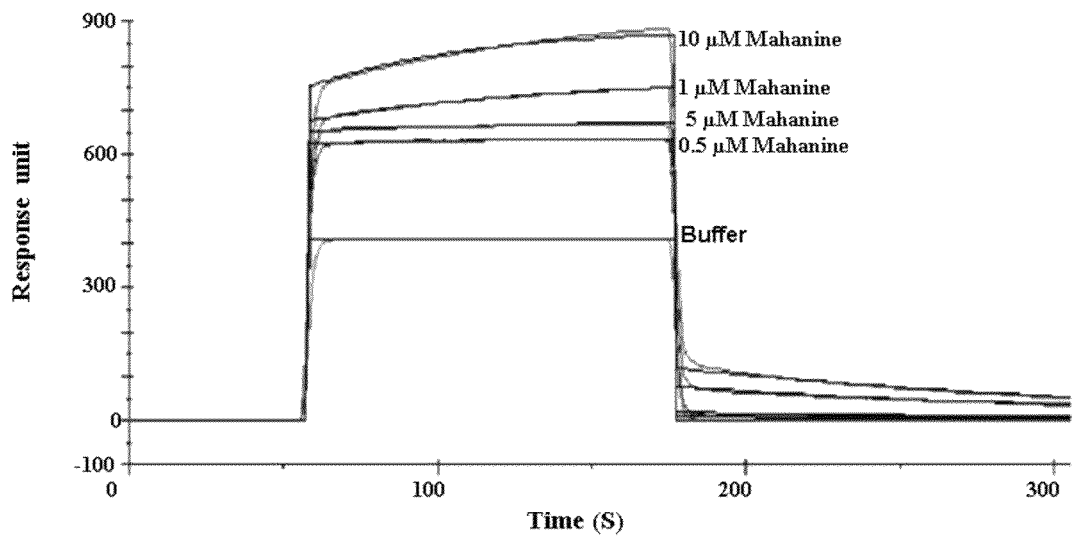
FIG. 22 shows the surface plasmon resonance sensorgram (SPR) of the binding of mahanine to Hsp90. Mahanine at different doses (0.5 µM, 1 µM, 5 µM, 10 µM) were added to immobilized human Hsp90 at a final concentration of 50 µg/ml. Coupling of Hsp90 to the CM5 sensor chip and measurement of SPR was performed as described in materials and methods.

The portion of the sensorgram which corresponds to the dissociation of mahanine from Hsp90 was analyzed by the BIA evaluation program 2.1 to obtain the dissociation rate (kd) (FIG. 22). The experimental data fits well with the single exponential kinetic model used. Some experiments were repeated at a flow rate of 5 µl/min to check the effect of possible rebinding. Rebinding and mass transfer limitation was also checked by the repetition of the experiments at lower levels of immobilized Hsp90. The identical results showed that these phenomena did not occur under the conditions we used. Using the corresponding kd values nonlinear curve fitting of the association phase of the corresponding sensorgram was carried out with the BIA evaluation program 2.1 to obtain association rate (ka). Dissociation constant (KD) for Hsp90-mahanine complex was calculated as the ratio of backward (6.21×10-3 S-1) and forward (1.24 S-1) rates (kd/ka) to get the value as 4.99 µM with maximum resonance ($R_{max}$) at a value of 198.90.

In Silico Molecular Modeling Data Revealed the Dissociation Between Hsp90-Cdc37

Figure 23:
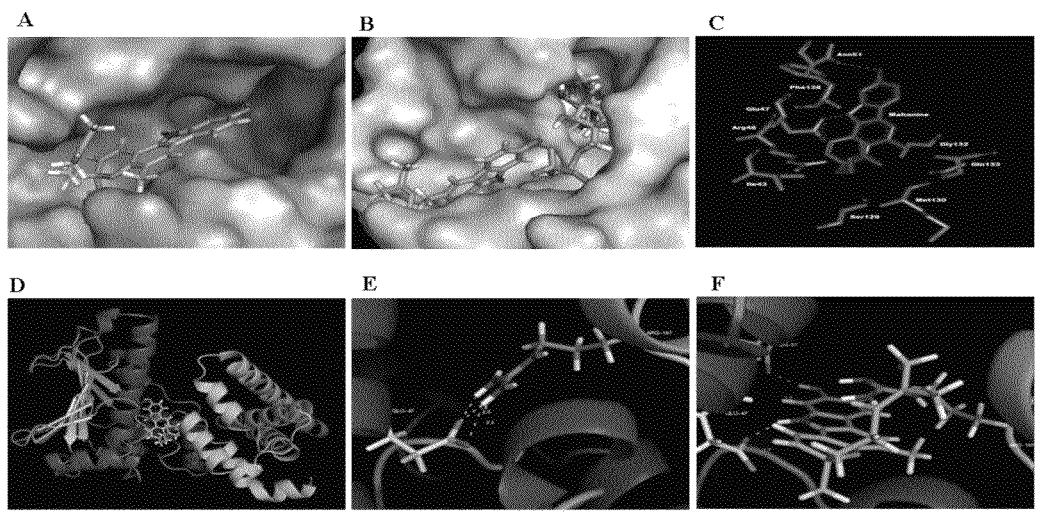
FIG. 23 shows molecular modeling studies of Hsp90 and Hsp90-Cdc37 complex with mahanine. (a) Binding site of mahanine in Hsp90. Mahanine is displayed in stick model and Hsp90 in surface view. (b) State of mahanine and ATP in Hsp90. Surface representation of Hsp90 where mahanine and ATP are in stick model. (c) Residues involved in interaction of mahanine with Hsp90. Hsp90 and mahanine is represented in stick model; sticks are colored by atom. Carbon=green in Hsp90 and pink in Cdc37. (d) Status of mahanine in Hsp90-Cdc37 complex. Ribbon display of Hsp90 (helices in red, sheets in yellow, loops in green) and Cdc37 (helices in cyan, loops in magenta) and mahanine in stick model. (e) Interaction of Hsp90 (Glu47) with Cdc37 (Arg167). Hsp90 and Cdc37 viewed in ribbon form where protruded side chain of residues are in stick model and colored by atom (carbon=yellow in Hsp90 and pink in Cdc37). (f) Disruption of interaction between Hsp90 and Cdc37 in presence of mahanine. Hsp90 and Cdc37 viewed in ribbon form where protruded side chain of residues and mahanine are in stick model and colored by atom (carbon=yellow in Hsp90, pink in Cdc37 and green in mahanine).

Molecular modeling shows mahanine binds to Hsp90 with a high binding affinity. The biomolecular observation was further corroborated by the molecular docking studies. Molecular modeling was used to examine the binding site of mahanine to Hsp90 which revealed that mahanine was bound to Hsp90 in a polar groove which was distinct from the ATP binding cavity (FIGS. 23A and B). Mahanine formed two hydrogen bonds with Hsp90, one with side chain oxygen of Glu47 through its NH group and other with side chain oxygen of Asn51 through its OH group. In addition, it showed hydrophobic interactions with Arg46, Ile43, Gly132, Gln133, Met130, Ser129, Phe138, Ile131 and Gly137 (FIG. 23C). Several docked conformations were taken into consideration for molecular dynamic simulation to select the best binding pose of mahanine with Hsp90. Molecular dynamics (MD) simulations were performed for 1 ns which showed that the complex was stable preserving the similar interactions between the protein and ligand. The most favorable pose of ligand with the protein has a binding energy of −7.6 Kcal/mol with a micro molar binding affinity ($K_D$=3.16 µM). Interestingly, the binding site of mahanine to Hsp90 is also the binding interface zone of Cdc37 with Hsp90 (FIG. 23D). We further examined whether the mode of binding of mahanine to the binding site of Hsp90 could disrupt the Hsp90-Cdc37 binding.

Molecular Modeling Reveals Disruption of Hsp90-Cdc37 Complex in Presence of Mahanine The MD simulation of Hsp90-mahanine-Cdc37 complex for 1 ns showed that the Hsp90-mahanine-Cdc37 complex was stable. Mahanine, being in the binding site, disrupted the hydrogen bonding interaction between Glu47 of Hsp90 and Arg167 of Cdc37 (FIGS. 23E and F). The empirical interaction energy of Hsp90-Cdc37 complex in presence of mahanine was −34.992 Kcal/mol and in absence of mahanine was −88.162 kcal/mol. This observation suggests that mahanine is interfering in the interaction between Hsp90 and Cdc37 and would significantly decrease the binding affinity of the co-chaperone, Cdc37 for Hsp90.

Mahanine Induces Time-Dependent Increase of Intracellular $Ca^{2+}$

Figure 24:
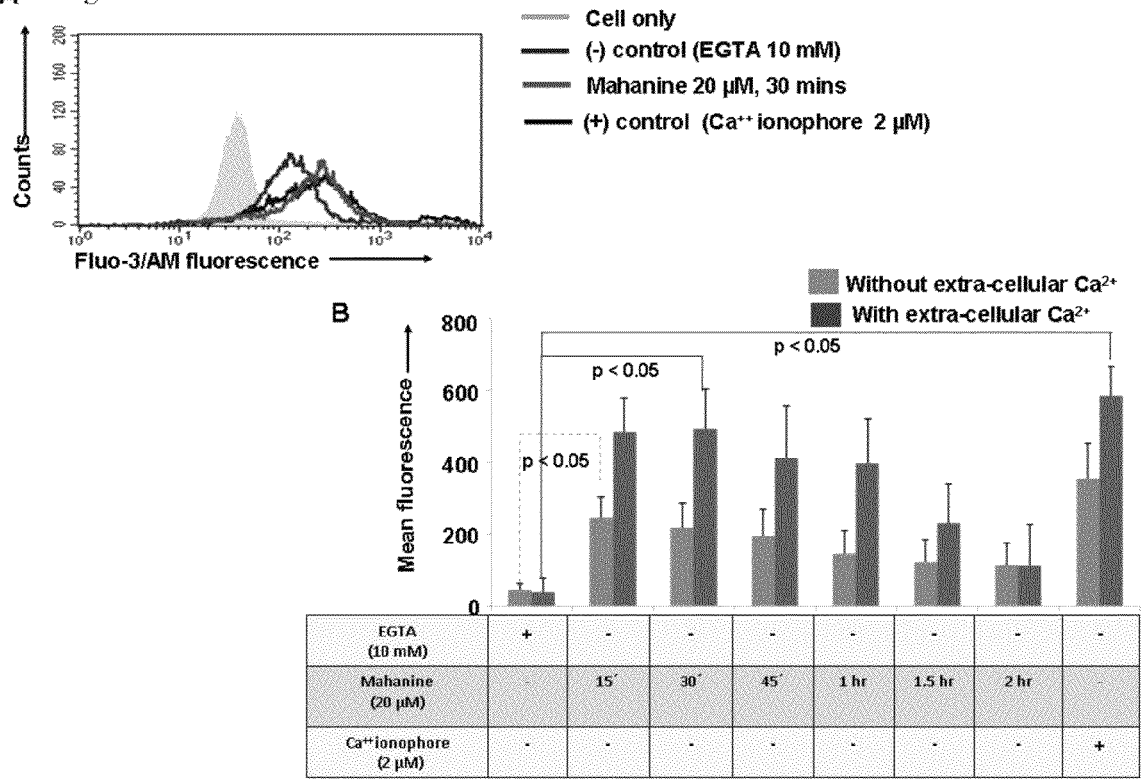
FIG. 24 shows Mahanine induced time-dependent increase of intracellular Ca$^{2+}$ in MIAPaCa-2. (a) Treatment with mahanine led to the enhancement of intracellular Ca$^{2+}$. EGTA (10 mM) and Ca$^{2+}$ ionophore (2 µM) served the purpose as negative and positive control respectively. (b) Time scanning disclosed mahanine mediated sudden and highest rise of intracellular Ca$^{2+}$ pool even without the presence of extracellular Ca$^{2+}$ (c) Confocal microscopy unveiled mahanine mediated ER stress in MIAPaCa-2 cells as evident by enhanced ER staining induced by dose dependent mahanine treatment after 18 hrs.
Figure 24:
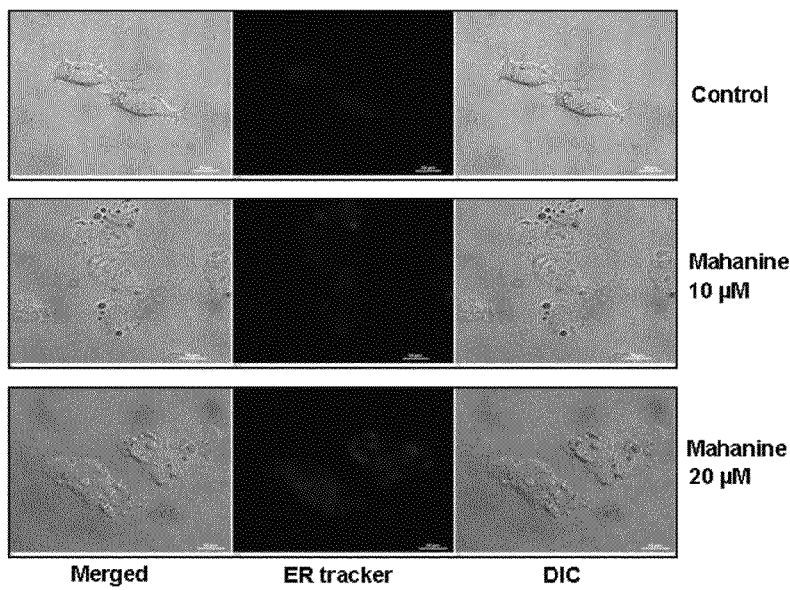

Since inhibition of chaperone by mahanine treatment can lead to the augmentation of protein load which can be resulted into the endoplasmic reticular (ER) stress within the cell. This ER stress can lead to the leaching out intra-cellular $Ca^{2+}$ from endoplasmic reticulum. Consequently, we next wanted to evaluate the intracellular $Ca^{2+}$ pool after mahanine treatment. Within 15 minutes of mahanine treatment enhance the intracellular $Ca^{2+}$ pool the maximum with and even without the presence of extra-cellular $Ca^{2+}$. The negative and positive control were done by using EGTA (10 mM) and $Ca^{2+}$ ionophore (2 µM) where it showed the lowest and the highest mean fluorescence intensity (MFI) respectively (FIGS. 24A and 24B).

Treatment with thapsigargin, an ER stress inducer by inhibiting ER $Ca^{2+}$ ATPase activity, has been recently proved to increase the fluorescent intensity of ER-Tracker Blue-White DPX after the ER staining with it. Results in FIG. 24C summarized the staining of MIAPaCa-2 cells with ER-Tracker Blue-White DPX dye after 18 hrs treatment with 10 µM and 20 µM mahanine. This dye is a photostable probe that is selective for the endoplasmic reticulum (ER) in live cells and the results confirmed that MIAPaCa-2 cells exhibited significantly increased blue staining compared with the control, suggesting the induction of ER stress. These results suggested that mahanine is an inducer release of $Ca^{2+}$ from the ER and activate ER stress in MIAPaCa-2 cells.

Mahanine Inhibits Pancreatic Adenocarcinoma Cell-Haptotaxis in Dose-Dependent Manner A number of Hsp90 client proteins are concerned with cell motility and invasion. In a scratch wound haptotaxis assay, higher invasive pancreatic carcinoma cell line, MIAPaCa-2 (FIG. 25A) and moderate invasive BxPC-3 (FIG. 25B) completed >40% wound closure within 6 hrs in vehicle control. The rate of cell migration decreases in dose dependent mode and the highest treated cells completed <5% of wound closure.

Figure 25:
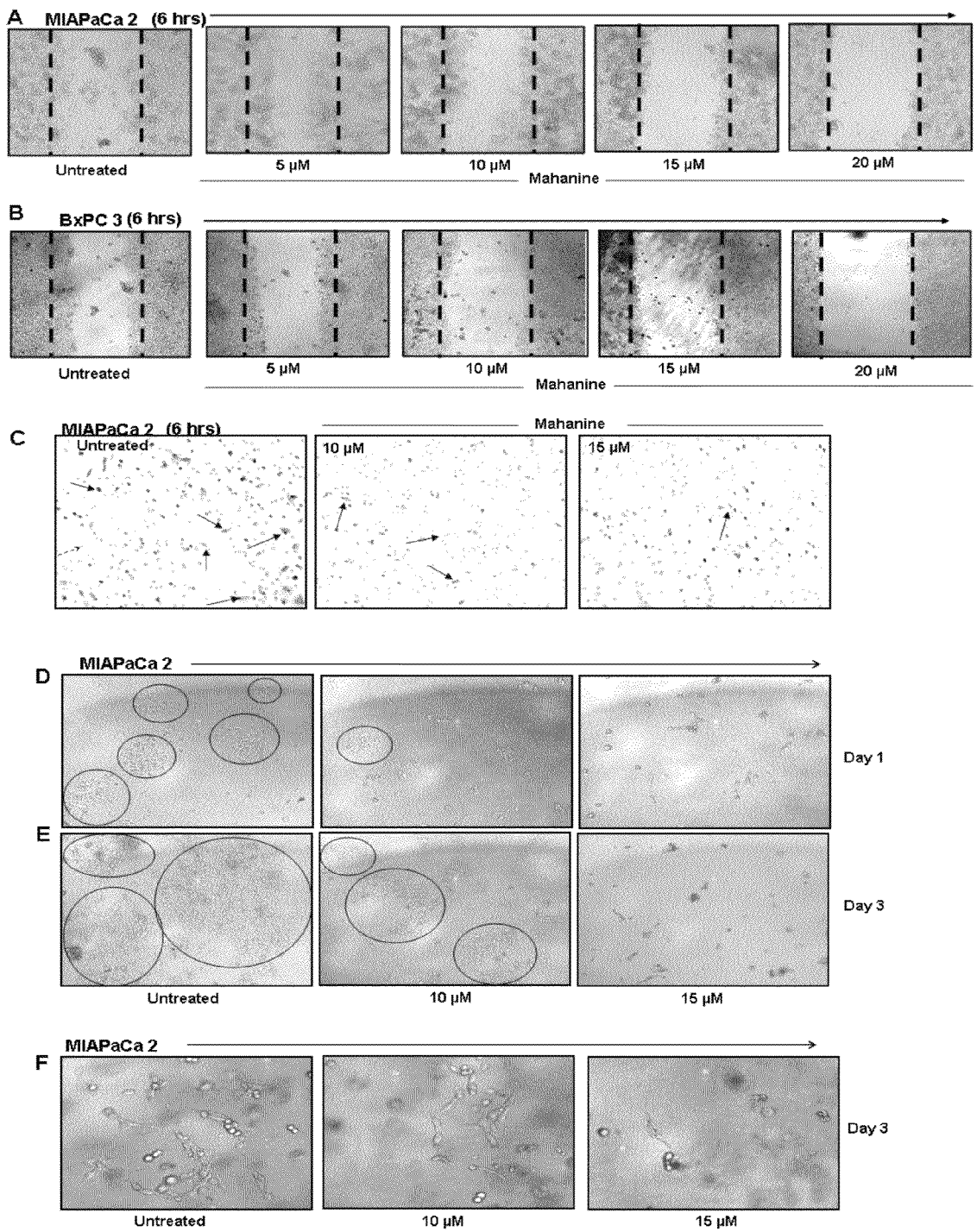
FIG. 25 shows Mahanine mediated inhibition of cell haptotaxis, chemo-migration, colony formation and tubular differentiation in pancreatic adenocarcinoma. (a) MIAPaCa-2 and (b) BxPC-3 showed >40% cell-migration in vehicle control where as highest treated cells showed only <5% migratory cells as revealed by the phase contrast microscopy. (c) Mahanine treated MIAPaCa-2 cells showed declination of EGF driven chemo migration in dose dependent manner. (d) and (e) mahanine treatment led to the dose dependent inhibition of in vitro colony formation after day 1 and day 3 respectively. (f) in vitro tubular differentiation assay demonstrated that mahanine treated MIAPaCa-2 cells were poorly differentiated after 3-day 3-D culture into matrigel.

Mahanine Inhibits In Vitro Migration of Highly Invasive Pancreatic Carcinoma Cell MIAPaCa-2 cells are highly invasive and belong to the highest grade (G-3) of primary pancreatic adenocarcinoma. However, the migration of MIAPaCa-2 was inhibited in a concentration dependent manner after 24 hrs exposure to mahanine. At ~0.6×$IC_{50}$ concentrations of 48 hrs (10 EGF-driven MIAPaCa-2 migration was reduced to 48.6% of controls where as nearly complete inhibition of cell migration was observed at ~1×$IC_{50}$ concentrations of 48 hrs i.e. 15 µM (FIG. 25C). However, PDGF and VEGF mediated MIAPaCa-2 chemo-migration showed almost identical results, more specifically, little less than that of the EGF mediated migration (data not shown).

Figure 26:
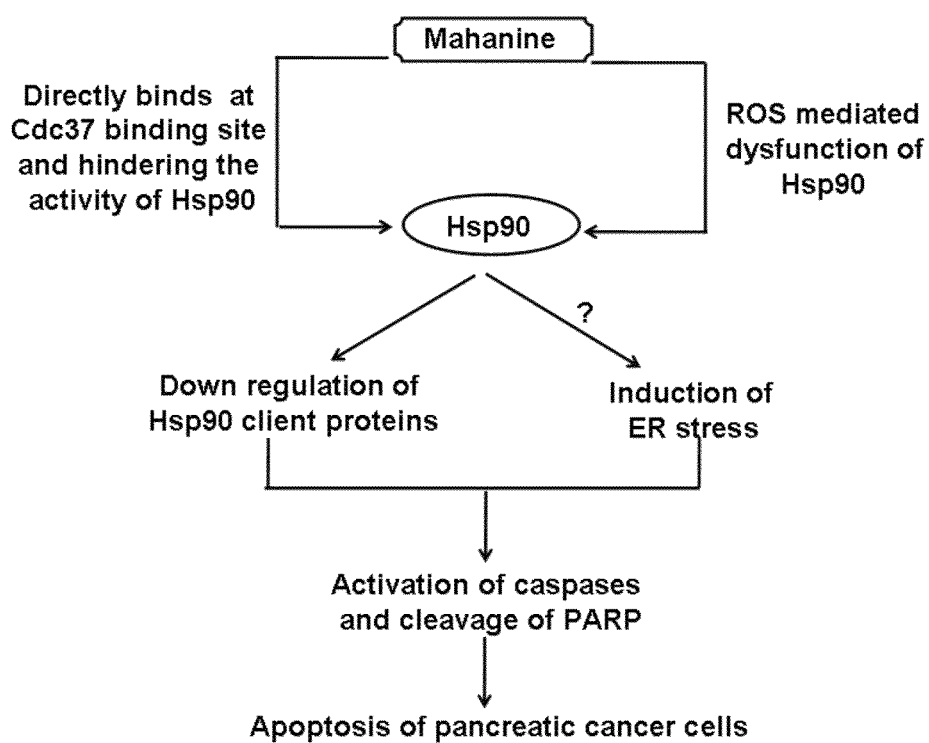
FIG. 26 shows a non-limiting schematic diagram of established pathway by mahanine mediated apoptosis through Hsp90 inhibition in pancreatic adenocarcinoma.

Mahanine also inhibited in vitro colony formation of MIAPaCa-2 on matrigel in a concentration-dependent manner within 24 hrs, with ~20% inhibition at 10 µM dose and colony formation absolutely inhibited at the 15 µM (FIG. 25D). Additionally, after 72 hrs enlarged colony size were seen in vehicle control as well as 10 µM treated cells though the treated cells showed significantly less number of cells in its colony. So far, cells treated with 20 µM concentration of mahanine could not colonize yet after 72 hrs incubation (FIG. 25E). Moreover, in vitro tubular differentiation assay showed that mahanine treated MIAPaCa-2 cells differentiated in dose responsive manner after 3-day 3-D culture onto matrigel (FIG. 25F). FIG. 26 provides a non-limiting schematic diagram of mahanine mediated apoptosis through Hsp90 inhibition in pancreatic adenocarcinoma.

EXAMPLES

Following examples are given by way of illustration therefore should not be construed to limit the scope of the invention.

Example 1

Source of *Murraya Koenigii* (Rutaceae)

The leaves of *Murraya koenigii* (Rutaceae family) were collected from different areas of West Bengal, India. Rutaceae family belonging plants contains high amount carbazole alkaloid which are biologically active. A voucher specimen has been deposited at the Department of Medicinal Chemistry, Indian Institute of Chemical Biology, Kolkata, India.

Example 2

Isolation and Purification of Mahanine and Dehydroxy-Mahanine from the Extract of *Murraya Koenigii* (Rutaceae) and Modification of Functional Group in Both of the Compound The fresh leaves of *Murraya koenigii* (1.5 kg) were extracted with methanol (5 L) in a mixture blender. The combined methanol extract was concentrated to dryness to give residue (68 g) and was tested for bioactivity. The methanol extract (50 g) was dissolved in 1.5 L of chloroform. In this solution add drop wise 10% HCl to recover the only alkaloid part. From a separating funnel we take the 10% HCl part and make it alkaline with liquid ammonia till pH=11.2. After precipitation, the precipitate was dissolved in EtOAc (500 ml) and evaporation of this solution yielded enriched alkaloids (6 gm). After that alkaloid part was subjected to repeated chromatography on silica gel [solvent: petrol-chloroform (9:1) and crystallization on petrol afforded several compounds. The most bioactive two of them are identified as mahanine (720 mg) and Dehydroxy-mahanine (750 mg).

Mahanine (100 mg) is stirred with methyl iodide (1.3 eqv.) for three hours in the presence of dry DMF and $K_2CO_3$ (1:1, 2 ml) to get the methylated mahanine. After formation of the product methylated mahanine was isolated by column purification and confirmed by mass spectrometry and NMR data analysis. Acetylated mahanine was prepared by stirring mahanine with dry pyridine and acetic anhydride for 6 hours. After complete the reaction the desired product was purified and identified by $^1H$ and $^{13}C$ NMR data analysis. Biotinylated mahanine was synthesized by dissolving mahanine in DMSO followed by adding 1 equivalent DMAP and 1 equivalent PFP-Biotin and stirred it at 37° C. for three hours. The product was purified by column chromatography and confirmed the structure by NMR data analysis.

Methylated dehydroxy-mahanine was prepared under stirring dehydroxy-mahanine with 3 equivalent of NaH and 1.3 equivalent of methyl iodide with dry DMF (2 ml) for three hours. After the reaction to deactivate the excess NaH saturated $NH_4Cl$ solution was added. The product mixture was worked up with saturated brine solution to isolate the methylated dehydroxy-mahanine.

Example 3

Culturing of Different Human Cancer Cell Lines

Human cervical cancer cell lines (HeLa, ME-180 and SiHa), brain tumor cell lines (U87MG, U373MG, U87MG EGFRvIII, T98G, A172 and LN229), lymphoid leukemia (MOLT-3, MOLT-4, REH and CEMC-7), myloid leukemia (K562), pancreatic cancer (MIAPaCa-2, AsPC-1, Panc-1 and Panc 10.05), lung cancer (A549) and colon cancer (HCT116 and SW480) cell lines from American Type Culture Collection, Manassas, Va., USA were grown in IMDM or RPMI (cell specific) Medium supplemented with 10% fetal bovine serum and 1% antibiotic-antimycotic. Cells were cultured in 37° C. in an atmosphere of 5% $CO_2$.

Primary Culture of Rat Neonatal Cardiomyocytes

The cardiomyocytes from 2-day-old neonatal rat were isolated. Briefly, heart was excised and minced in pre warmed (37° C.) Ads buffer (1.2M NaCl, 198 mM HEPES, 54 mM KCl, 8.3 mM $MgSO_4$, 55.4 mM glucose, 95 mM $NaH_2PO_4$), digested in typeII Collagenase 0.05% and Pancreatin in 3-successive digestions of 15 minutes each. Supernatant was pooled and cells palleted at 2000 g, 10 minutes. Cells were resuspended and plated in collagen coated T-25 flaks in Medium-199 enriched with 10% Fetal Bovine Serum and 1% antibiotic-antimycotic.

Primary Culture of Rat Neonatal Hepatocyte

The hepatocytes from 2-day-old neonatal rat were isolated. Briefly, The liver were perfused through the portal vein with a calcium-free solution consisting of 150 mM NaCl, 2.8 mM KCl, 5.5 mM glucose, and 25 mM HEPES (pH 7.6) for 10 min, followed by mincing and digestion in DMEM containing 0.05% collagenase type IV for 30 minutes. The cells were centrifuged (2000 g, 10 minutes) and dispersed in DMEM enriched with 10% fetal Bovine Serum, 1% antibiotic-antimycotic.

Primary Culture of Neonatal Rat Skeletal Muscle

The skeletal muscles from 2-day-old neonatal rat were isolated. Briefly, Soleus muscles were dissected minced and digested with 0.2% Type II Collagenase and 0.05% trypsin in Phosphate buffered Saline (PBS) pH 7.4, 0.15 M NaCl. The dispersed skeletal muscle cells were centrifuged (1000 g, 10 minutes) washed and resuspended in Phosphate buffered Saline (PBS) with 1% antibiotic-antimycotic. Cells were pre-incubated for 30 minutes at 37° C., 95% air/5% $CO_2$. The floating muscle cells were plated on collagen coated T-25 flaks in Dulbecco's modified Eagle Medium enriched with 10% Fetal Bovine Serum and 1% antibiotic-antimycotic.

Example 4

Measurement of Cell Survivility by MTT Assay

Viability of cancer cell lines after treatment as at the indicated times was determined by MTT assay. Briefly, 10,000 cells were plated in triplicate in 96 well plates and incubated for 24 and 48 hours in complete media in presence of varying dose of mahanine (0-50 µM). 100 ug MTT was added in each well. Incubate the plate for 1-4 hours at 37° C. and humidified 5% $CO_2$ atmosphere. Absorbance was recorded at 550 nm with 96 well plate readers.

Example 5

Flow Cytometric Analysis of Apoptosis and Mitochondrial Depolarization

U87MG, LN229, HeLa, SiHa and ME180 (1×10$^6$ cells) cells were cultured in 6-well plates in presence or absence of Mahanine (25 µM) for 24 hrs. Cells were washed in PBS, incubated with 7-Aminoactinomycin D (7-AAD) at 4° C. for 20 min and processed. Data acquisition was done on a FACSCalibur flow cytometer (BD) at excitation wavelength at 488 nm and emission wavelength at 647 nm and analyzed with CellQuestPro software.

For the mitochondrial depolarization detection assay both the mahanine treated and untreated cells are stained with JC-1 (25 µg/ml) at 37° C. for 20 min and processed for flow cytometric analysis.

Example 6

Electrophoresis and Immunoblotting and Immunoprecipitation

Different human cancer cells (1×10$^6$ cells) were incubated with complete medium alone or with different dose of Mahanine (10-20 µM) as indicated. Cells were detached using trypsin-EDTA solution. They were collected by centrifugation at 1500 g for 10 mins and lysed by sonication. Aliquots containing 60 µg total cellular protein were separated by 10% SDS-PAGE and transferred to nitrocellulose membrane (MILIPORE, Bedford, Mass., USA). Membrane was blocked with blocking buffer for 1 hour at room temperature and probed with desired primary antibody Hsp90, Hsp70, Hsp40, p23, HOP, Cdc37, B-Raf, Stat-3, Bcl-xl, Akt, PARP, β-actin (Cell signaling technology, USA) and caspase-3 (Santa Cruz, USA), caspase9, cytochrome c (cell signaling technology, USA) for overnight at 4° C. followed by HRP conjugated secondary antibody and detected by ECL. For the detection of association of the Hsp90-Cdc37, Hsp90-p23 and Hsp90-HOP, total cell lysate (400 µg) was treated with anti-Hsp-90 antibody (1:100 dilutions) and incubated overnight at 4° C. The chaperonic complex was resolved by SDS-PAGE (10%), transferred and probed separately with anti-Cdc37, anti-HOP, anti-p23 and anti-Hsp-90 antibodies. In the few immunoprecipitation experiments anti-Cdc37 used as precipitating antibody and Hsp90 was used as detection antibody. For the proteasomal inhibition assay cells were pretreated with 10 µM MG132 for 1 hr and then cells are exposed in 20 µM mahanine for 24 hrs. For proteasomal inhibition assay at 6 hrs incubation in MIAPaCa-2, cells were pre-incubated with 20 µM MG132 for 1 hr and then cells were exposed in 30 µM mahanine.

Example 7

In Vivo Experiment, there was No Indication of any Toxicity in Compound Treated Mice (Table 2A, 2B)

TABLE 2A

| BIOCHEMICAL ANALYSIS | SGOT (Unit/ml) | SGPT (Unit/ml) | Urea (gm/dl) | Creatinine (gm/dl) |
|---|---|---|---|---|
| Control mice | 147.5 | 32.0 | 35.4 | 3.82 |
| Treated mice | 174.0 | 34.7 | 48.6 | 3.72 |

TABLE 2B

| BLOOD ANALYSIS | RBC | WBC | Hb (gm/dl) |
|---|---|---|---|
| Control mice | 1323 | 112 | 13.25 |
| Treated mice | 1513 | 139 | 13.64 |

Animals were examined for 1 month after the administration of acute toxic dose (150 mg/kg/day); there was no change in behavior, feeding habit, total body mass and in number of biochemical and haematological parameters.

Example 8

Study of In Vivo Bioavailability of Mahanine and Dehydroxy-Mahanine

EtOAc extract of *Murraya koenigii* was orally fed to normal healthy Balb/c (100 mg/kg body weight) and blood was collected from retro orbital plexus after 30 min interval by glass capillary. Control blood was collected from the mice before the injection of extract. The Institutional Animal Ethical Committee had approved the study. Blood serum was isolated and the serum protein was separated by centrifugation in ice-cold acetone. Supernatant was evaporated to dryness and residual part was dissolved in minimum volume of MeOH and injected into the HPLC column. From the HPLC peak profile the bioavailability of mahanine and dehydroxy-mahanine was determined. in vivo bioavailability assay indicated that mahanine and dehydroxy-mahanine both are easily absorbable compound with in the blood circulation.

Example 9

ATP Binding Assay

5 µg of purified Hsp90α and Hsp90β were pre-incubated separately on ice with 200 µL incubation buffer (10 mM Tris-Hcl, 50 mM KCl, 5 mM $MgCl_2$, 2 mM DTT, 20 mM $Na_2MoO_4$, 0.01% NP40, pH 7.5) containing mahanine or 17-AAG and incubated for 30 mins on ice. After the incubation, 25 µL pre-equilibrated γ-phosphate ATP sepharose added and again incubated at 37° C. with frequent agitation.

Sepharose subsequently washed and analyzed by SDS-PAGE. Then the blot was probed with anti Hsp90 antibody and developed by ECL.

Example 10

Interaction Studies Using SPR Technique

All the solutions were passed through a 0.22 micron Millipore filter and de-gassed in vacuum for 6-7 minutes at room temperature. For coupling Hsp90 to the SPR sensor chips, 400 µl (50 µg/ml) human Hsp90 was dialysed over night at 4° C. against coupling buffer containing 5 mM $Na_2HPO_4$, pH 7.4 and 150 mM NaCl to remove Tris, which interferes with the coupling. Before coupling, carboxymethyl-dextran sensor chips (CM5, Lot 1170768, Biacore, Upsala Sweden) were incubated with running buffer containing 10 mM HEPES, pH 7.4, 0.15 M KCl and 0.001% Tween-20 to prevent the unspecific binding of proteins to the capillaries in a BIAcore apparatus for 10 minutes at 25° C. at a flow rate of 5 µl/min. The carboxymethyl-dextran coated sensor chip was activated with 1-ethyl-3-[3-dimethylaminopropyl]-carbodiimide (200 mM) and N-hydroxy-succinamide (50 mM) in Milli-Q deionized water for 5 minutes at 25° C. Human Hsp90 (50 µg/ml) was coupled to the chip in a buffer containing 20 mM Na-acetate, pH 4.0, for 10 minutes at 25° C. The remaining active sites of the resin were inactivated by incubation with ethanolamine-HCl (1M) solution for 10 minutes at 25° C. After coupling, non-covalently bound Hsp90 was removed by two brief (two minutes) fluxes of HCl (20 mM). Mahanine was dissolved in running buffer at various concentrations (0.5, 1, 5, 10, 20 and 30 µM) and injected to run over Hsp90 coated CM5-sensor chip at a flow rate of 10 µl/minute. The association mainly occurred on 1, 5, and 10 µM doses but at 20-30 µM dose a saturation occurred.

Example 11

Molecular Modeling Studies

Preparation of Receptor Model
The structural coordinates of the human Hsp90 and Cdc37 protein were obtained from NMR derived structure of the complex in the Protein Data Bank (2K5B). The protein structures were separated and cleaned by removing water molecules before docking.
Preparation of Ligand Model
The structure of Mahanine was built using Builder module of molecular modeling software suite InsightII (2005) of Accelrys (San Diego, Calif.). The structure was optimised with repeated energy minimization and molecular dynamics simulations using DISCOVER module. Energy minimization was performed alternatively with steepest descent and conjugate gradient methods (200 steps each using cff91 force field). Molecular dynamics simulation run was done with 10,000 steps of 1 fs after 1000 steps of equilibration with a conformation sampling of one in 100 steps at 300K. At the end of the molecular dynamics simulation, the lowest potential energy conformation was picked using ANALYSIS module of Insight II for further energy minimization. The optimised structure was used for docking studies.

Molecular Docking

Molecular Docking was performed between individual proteins and mahanine using Autodock 4.2. In our docking studies, Hsp90 protein was used as target and mahanine as ligand and flexible docking was performed. Next, docking was done between Cdc37 and mahanine. Protein structures were prepared by adding hydrogens, non-polar hydrogens were merged and gastegier charges were assigned. Similarly, gastegier charges computed by Autodock tool were used on each atoms of the ligand. AutoTors utility was used to define torsional degrees of freedom for the ligand. Autogrid was used to perform grid map settings. The dimension of the grid was prepared at 60×60×60 with the spacing between the grid points at 0.375 Å. Lamarkian genetic algorithm was used to perform docking simulation, with an initial population of 150 randomly placed individuals, maximum number of 2, 50,000 energy evaluation, 150000 generations, mutation rate of 0.02, a cross over rate of 0.8 and an elitism value of 1 was used. 50 docking runs were performed. Pseudo-Solis and Wets algorithm was used for local search method. Finally, the resulting docked conformations were clustered together on the basis of root mean square deviation (RMSD) tolerance of 1.5 Å and represented by most favorable free energy of binding.

Molecular Dynamic Simulation

In order to evaluate the absolute binding energy of a ligand to the receptor molecule, two MD simulations were performed using Gromacs-3.3.2 package, applying Gromos 96 force field, one of the solvated ligand-protein complex and the other ligand free in solution. The ligand bound and unbound complex was solvated in an octahedron box of SPC water molecule with a minimum solute-wall distance of 10 Å. Appropriate number of Na+ ions was added to neutralize the charge of the system. Each of the solvated system was energy minimized using steepest descent method for 1000 steps. The minimized complex was then subjected to MD simulations in two steps. At first, we performed 80 ps of MD at 300K with position restrained dynamics (equilibration) in order to ensure that the solvent molecules were balanced around the protein. The MD simulation was performed with a periodic boundary condition in the NPT ensemble at 300K and 1 atmosphere pressure using Berendsen temperature and pressure coupling. The LINCS algorithm was applied to fix all covalent bonds containing hydrogen atom, a time step of 1 fs was used and cut off distances for electrostatic and non bonded interactions were set at 12 Å and 14 Å respectively. The non-bonded pair list was updated every 10 steps and conformation was stored every 1 ps. The parameterization of the ligand was carried out in Dundee PRODRG server using Gromos 96 force field. To analyze the structures generated after the MD steps, VMD software was used.

Binding Free Energy Calculation

The free energy of binding of ligand to the protein was calculated using Linear Interaction Energy (LIE) method as described by Aqvist et al. The average interaction energy between the ligand and its surroundings was calculated using g_lie command incorporated in the Gromacs-3.3.2 package. g_lie uses linear interaction energy method to calculate free energy of binding of a ligand to its receptor as a linear combination of differences in the average "ligand-solvent" interaction between bound and free state of ligand.

$$\Delta G_{bind} = \frac{1}{2}\Delta \langle V^{el}_{l-s} \rangle + \alpha \Delta \langle V^{vdw}_{l-s} \rangle$$

Here, Δ refers to the bound and free simulation differences and l-s refers the ligand-solvent interaction (solvent includes protein also). The value ½ is for the electrostatic term and α=0.18 is for the van der Waals energy. The binding free energy ($\Delta G_{bind}$) value was used to calculate the binding constant ($K_a$) using the formula $$\Delta G_{bind} = -RT \ln K_a$$

The $K_d$ (dissociation constant) was calculated as $1/K_a$.

Protein—Protein Interaction Energy Calculation

Using Accelry's Discovery studio 2.5, the Hsp90-mahanine docked complex was superimposed with Hsp90-Cdc37 complex (2K5B) and replaced with Hsp90 protein. The Hsp90-mahanine-Cdc37 complex was typed with Charm 27 force field and solvated in an octahedron box of 20 Å by adding equal number of counter ions. The solvated complex was energy minimised with Steepest Descent followed by Conjugate Gradient method (200 steps each). The sequence of minimization was repeated twice. From simulation module, the interaction energy of Hsp90 and Cdc37 in presence and absence of mahanine was calculated.

Example 12

In Vitro Intracellular $Ca^{2+}$ Measurement

MIAPaCa-2 cells ($3 \times 10^6$), treated with mahanine, were washed in 1× Hanks Balanced Salt Solution (HBSS) [Gibco, Invitrogen Corporation, USA] and then loaded with Fluo-3/AM (2 μM, Calbiochem, Germany) in HBSS containing 1.26 mM $CaCl_2$. The cells were incubated at 37° C. for 30 min in dark with gentle agitation. All extracellular Fluo-3/AM was removed by two-three times washing in aforesaid buffer. The level of cytoplasmic $Ca^{2+}$ within Fluo-3/AM loaded MIAPaCa-2 was determined in time dependent manner in the absence and presence of $CaCl_2$ (1.26 mM $CaCl_2$).

Example 13

Confocal Microscopy

MIAPaCa-2 cells were seeded in 8 chambered polystyrene culture slide [BD Falcon, USA] at $5 \times 10^3 \neg$ cells per well in RPMI-1640 medium supplemented with 10% FBS. After 24 hrs of seeding, cells were exposed to different concentration of mahanine along with vehicle control. Cells were washed with 1× Hanks Balanced Salt Solution (HBSS) after 18 hrs of incubation and processed for ER staining. Pre-warmed ER-Tracker Blue White DPX (Molecular Probes) was added to the cells at 500 nM working concentration and incubated for 30 mins at 37° C. at 5% $CO_2$ incubator. The loading solution was removed and cells were then washed again in HBSS and samples were analyzed using confocal laser scanning microscope (NICON A1-R, NICON, Japan). Images were recorded using 60×/1.40 oil plan Apo-N objectives at calibrated magnification.

Example 14

Scratch-Wound Assay

Highly and moderately invasive pancreatic cancer cell lines, MIAPaCa-2 and BxPC3 ($1 \times 10^6$/ml/well) were cultured to >90% confluence in 6 well plate. Consequently, cell were rinsed with PBS and starved in low serum media (2 ml containing 0.5%-0.1% serum in RPMI-1640 for MIAPaCa-2 and BxPC-3) for overnight. On the following day, three separate scratch-wounds were made through the confluent cells. Scratched plate was rinsed with PBS and replaced with serum starved media containing successive doses of mahanine or EtOH for 6 hrs. Picture was taken by using phase contrast at 10× accordingly.

Example 15

Transmigration Assay

MIAPaCa-2 cells were treated with mahanine in dose responsive manner for 24 hrs. Afterward, different growth factors (VEGF, EGF and PDGF) were dissolved in medium at a final concentration of 20 ng/ml and added into the outer well of the 24-transwell plate (PromoCell Heidelberg, Germany) as per manufacturer instruction. Mahanine-pretreated cells ($5 \times 10^4$ cells/well/500 µl) were added into the insert and incubated at in a humidified incubator (37° C., 5% CO2) for 6 hours and subsequently invaded cells were fixed with chilled methanol and stained with 0.1% crystal violet. Random fields were photographed and quantified under the phase contrast microscope.

Example 16

In Vitro Colony Formation Assay

MIAPaCa-2 cells were propagated under the mahanine treatment in dose responsive manner for 24 hrs and then seeded ($2 \times 10^4$ cells/well/100 µl) onto 24-well cell culture plate coated with matrigel (1:2 matrigel). After 24 hrs of incubation, different microscopic fields were selected arbitrarily and captured under phase contrast microscope. Cells >30 were considered as a single colony for representation.

Example 17

In Vitro Tubular Differentiation Assay

To investigate the influence of mahanine on tube formation of pancreatic cancer cells we performed in vitro tubular differentiation assay. Briefly, $1 \times 10^4$ cells/100 µl, pretreated with mahanine, mixed with matrigel (already diluted with medium in 1:2 ratio) and coated in 24 well-plate and 3D-cultured until the tubular differentiation.

ADVANTAGES OF THE INVENTION

1. The main component plant *Murraya koengii* is abundantly available plants throughout India.
2. Novel purification protocol costs less and quick isolation.
3. Total yield of mahanine and dehydroxy-mahanine are high in EtOAc extract, which may be a useful combination for cancer treatment.
4. Pharmacokinetics study indicated that mahanine and dehydroxy-mahanine are easily absorbable component in blood stream and there is no production of secondary metabolites the native form of mahanine and dehydroxy-mahanine are bioactive form.
5. Mahanine showed anti-cancer activity in low dose ($IC_{50}$ lied between 12-17 µM after 48 hr treatment) against glioma and cervical cancer cell lines whereas Mahanimbine exhibited $IC_{50}$ being 30-50 µM against cancer cells.
6. Normal cells [heart, liver, muscle and peripheral blood mononuclear cells (PBMC)] showed minimum sensitivity towards mahanine indicated by in vitro testing.
7. Vero cells (proliferating normal cells) are less sensitive towards mahanine indicated by in vitro testing.
8. WI38 cells (normal human lung fibroblast cells) exhibited minimum sensitivity upto 50 µM towards mahanine indicated by in vitro testing.
9. Mahanine showed minimum toxic effects in vivo indicating that mahanine is nontoxic towards nonspecific tissues of athymic nude mice model.
10. Combination therapy with mahanine reduced dose of highly toxic two known anticancer agents (cisplatin and paclitaxal).
11. Mahanine could overcome the EGFRvIII mutation, which is the most lethal and difficult to treat cancer cells.
12. EtOAc extract was also potent to induce cell death in glioma (T98G) and cervical cancer (HeLa) and $IC_{50}$ being 140 and 134 µg/ml respectively.
13. Multiple administration modes (oral, intravenous, intramuscular or subcutaneous rout) were available of these active components for the in vivo treatment.
14. The main component plant *Murraya koengii* is abundantly available edible plants throughout India.
15. Novel purification protocol of the purified compound mahanine costs less and quick isolation in high yield.
16. The purified herbal compound, mahanine is stable in room temperature and after dissolving in ethanol the compound can be stably stored in −20° C. for >6 months.
17. Pharmacokinetics study indicated that mahanine is easily absorbable component in blood stream and there is no production of secondary metabolites the native form of mahanine are bioactive form.
18. The compound, mahanine, is isolated from an edible plant, so, it behaves like a nontoxic agent towards nonspecific tissues and body mass.
19. Mahanine showed anti-cancer activity in low dose ($IC_{50}$ lied between 11-14 µM after 48 hr treatment) against glioma, cervical and pancreatic cancer cell lines.
20. Vero cells (proliferating normal monkey kidney cell line) are less sensitive towards mahanine indicated by in vitro testing.
21. Mahanine showed minimum toxic effects in vivo indicating that mahanine is nontoxic towards nonspecific tissues of athymic nude mice model.
22. Mahanine showed orthotopic pancreatic tumour growth inhibition in athymic nude mice model.
23. Hsp90 chaperonic activity is predominant in majority of cancer and it folds and activates many onco-proteins, which are responsible for cancer initiation and progression. Mahanine targets Hsp90 and as well as all the related onco-proteins are degraded and deactivated. So, mahanine can inhibit cancer by inhibiting broad spectrum of oncoprotein inhibition.
24. There are very few compounds studied which can block the ATP binding site of the Hsp90, but mahanine can disrupt the Hsp90-Cdc37 complex and thus disfunctioning the Hsp90's chaperonic function.
25. Most of the Hsp90 inhibitory compounds have solubility, lesser in vivo efficacy, hepatotoxicity problems. Mahanine can be a better herbal replacement against these compounds.
26. Till date, FDA has not approved any Hsp90 inhibitor to come into the market. As Mahanine is isolated from an edible plant, it has minimal toxicity towards the normal cells and tissues and thus could be considered as a potent, less toxic Hsp90 inhibitor.
27. ATPase activity is a cellular obligation for proper cell functioning. Targeting the ATP binding pocket of Hsp90 is a poor approach to inhibit its function as there are several cellular kinases may have analogous ATP binding site for the execution of their activity. Mahanine can overcome this flaw, hindering the chaperonic function of Hsp90 by avoiding the typical ATP/ADP cycle, just by disrupting chaperone-cochaperone association.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:

1. A process for the isolation of compound of general formula 1

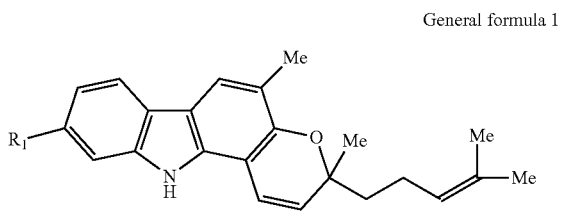

General formula 1 wherein $R_1$=H mahanimbine (1a) or $R_1$=OH mahanine (1b);

from *Murraya koeniigii*, said process comprising the steps of:
  i. extracting leaves of *Murraya koeniigii* with methanol followed by concentrating to obtain residue;
  ii. dissolving the residue as obtained in step (i) in a solvent followed by adding 8 to 10% acid;
  iii. separating the acid soluble part from the mixture as obtained in step (ii) and making the remaining solution alkaline to obtain a precipitate;
  iv. dissolving the precipitate as obtained in step (iii) in ethyl acetate followed by evaporating to obtain an alkaloid; and
  v. subjecting the alkaloid as obtained in step (iv) to repeated chromatography on silica gel using petrol-chloroform solvent as eluent followed by crystallization on petrol to obtain the compound of general formula 1.

2. The process as claimed in step (ii) of claim 1, wherein the acid used is selected from the group consisting of HCl, $H_2SO_4$, $CH_3COOH$, and $HNO_3$.

3. The process as claimed in claim 1, wherein the yield of the compound is in the range of 10 to 40% of methanolic extract.

4. The process as claimed in step (ii) of claim 1, wherein the solvent used is selected from the group consisting of chloroform, diethylether, and ethylacetate.

5. The process as claimed in claim 1, wherein compound 1a exhibits in vitro anticancer activity against human cancer cell lines selected from the group consisting of lymphoid cell lines, myeloid cell lines, glioma cell lines (U373MG, U87MG, LN229, T98G, A172), cervical cell lines (HeLa), pancreatic cell lines (Panc10.05, Panc1, AsPC1, MIAPaCa-2), colon cell lines and lung cancer cell lines (A549).

6. The process as claimed in claim 1, wherein compound 1b exhibits in vitro anticancer activity against human cancer cell lines selected from glioma cancer cell line (U373MG, U87MG, LN229, T98G, A172) or cervical cancer cell line (HeLa).

7. The process as claimed in claim 5, wherein the compounds 1a and 1b inhibit cell proliferation in glioma and cervical cancer cells at $IC_{50}$ in the range of 10-20 μM and 30-50 μM, respectively.

8. The process as claimed in claim 5, wherein the compound 1b hinders the Hsp90's chaperonic activity without hampering ATP binding site.

9. The process as claimed in claim 6, wherein the compounds 1a and 1b inhibit cell proliferation in glioma and cervical cancer cells at $IC_{50}$ in the range of 10-20 μM and 30-50 μM, respectively.

10. The process as claimed in claim 6, wherein the compound 1b hinders the Hsp90's chaperonic activity without hampering ATP binding site.

* * * * *

UNITED STATES PATENT AND TRADEMARK OFFICE
CERTIFICATE OF CORRECTION

PATENT NO. : 8,637,679 B2  
APPLICATION NO. : 13/416930  
DATED : January 28, 2014  
INVENTOR(S) : Chitra Mandal et al.

Page 1 of 1

It is certified that error appears in the above-identified patent and that said Letters Patent is hereby corrected as shown below:

In the Claims

Column 29, Claim 1, Line 37, replace "Murraya koeniigii" with --Murraya koenigii--;
Line 39, replace "Murraya koeniigii" with --Murraya koenigii--.

Signed and Sealed this
Thirteenth Day of May, 2014

Michelle K. Lee
*Deputy Director of the United States Patent and Trademark Office*